(12) United States Patent
Khurana et al.

(10) Patent No.: US 11,590,094 B2
(45) Date of Patent: Feb. 28, 2023

(54) FIXED DOSE COMBINATION FORMULATIONS FOR TREATING PAIN

(71) Applicant: Nevakar Injectables Inc., Bridgewater, NJ (US)

(72) Inventors: Varun Khurana, Raritan, NJ (US); Tushar Hingorani, Bridgewater, NJ (US); Jack Martin Lipman, West Milford, NJ (US); Kumaresh Soppimath, Skillman, NJ (US)

(73) Assignee: NEVAKAR INJECTABLES INC., Bridgewater, NJ (US)

( * ) Notice: Subject to any disclaimer, the term of this patent is extended or adjusted under 35 U.S.C. 154(b) by 121 days.

(21) Appl. No.: 16/644,022

(22) PCT Filed: Sep. 27, 2018

(86) PCT No.: PCT/US2018/053195
§ 371 (c)(1),
(2) Date: Mar. 3, 2020

(87) PCT Pub. No.: WO2019/067768
PCT Pub. Date: Apr. 4, 2019

(65) Prior Publication Data
US 2020/0246294 A1 Aug. 6, 2020

Related U.S. Application Data

(60) Provisional application No. 62/564,699, filed on Sep. 28, 2017.

(51) Int. Cl.
*A61K 31/197* (2006.01)
*A61K 31/167* (2006.01)
(Continued)

(52) U.S. Cl.
CPC .......... *A61K 31/197* (2013.01); *A61K 31/167* (2013.01); *A61K 31/192* (2013.01); *A61K 45/06* (2013.01)

(58) Field of Classification Search
None
See application file for complete search history.

(56) References Cited

U.S. PATENT DOCUMENTS 6,451,857 B1 9/2002 Hurtt et al.
2007/0281927 A1 12/2007 Tyavanagimatt et al.
(Continued)

FOREIGN PATENT DOCUMENTS

KR 1020130049178 A 5/2013
WO 2015157738 A1 10/2015
(Continued)

OTHER PUBLICATIONS

Alayed, et al., "Preemptive use of gabapentin in abdominal hysterectomy: a systematic review and meta-analysis," Obstet Gynecol., Jun. 2014;123(6):1221-9.
(Continued)

*Primary Examiner* — Sudhakar Katakam
*Assistant Examiner* — Jennifer C Sawyer
(74) *Attorney, Agent, or Firm* — Umberg Zipser LLP

(57) ABSTRACT

Fixed-dose combination drugs comprising an NSAID as a first drug component and a GABA-type calcium channel blocker as a second drug component are contemplated. Further contemplated aspects also include methods of administration of combination drugs and drugs contained herein.

9 Claims, 18 Drawing Sheets

| IR + SR | |
|---|---|
| Pregabalin | Acetaminophen |
| 25 mg | 650 mg |
| 37.5 mg | 650 mg |
| 50 mg | 650 mg |

- Pre-Op Formulation
- Pregabalin will be released immediately
- Acetaminophen will be sustained released over the duration of 8 hrs.
- Two tablets taken three times a day.

| SR + SR | |
|---|---|
| Pregabalin | Acetaminophen |
| 25 mg | 650 mg |
| 37.5 mg | 650 mg |
| 50 mg | 650 mg |

- Pre-Op Formulation
- Acetaminophen and Pregabalin will be sustained released over the duration of 8 hrs.
- Two tablets taken three times a day.

| IR + IR | |
|---|---|
| Pregabalin | Acetaminophen |
| 12.5 mg | 500 mg |
| 25 mg | 500 mg |
| 37.5 mg | 500 mg |

- Pre-Op Formulation
- Acetaminophen and Pregabalin will be released immediately.
- Two tablets taken four times a day.

(51) Int. Cl.
  *A61K 31/192* (2006.01)
  *A61K 45/06* (2006.01)

(56) References Cited

U.S. PATENT DOCUMENTS

| | | | |
|---|---|---|---|
| 2008/0020039 A1* | 1/2008 | Parikh | A61K 31/485 424/472 |
| 2015/0017267 A1 | 1/2015 | Guedes et al. | |
| 2015/0140090 A1 | 5/2015 | Kawai et al. | |
| 2016/0243134 A1 | 8/2016 | Hoyle et al. | |
| 2017/0273896 A1* | 9/2017 | Odidi | A61K 9/5042 |
| 2017/0290793 A1 | 10/2017 | Khurana et al. | |

FOREIGN PATENT DOCUMENTS

| | | |
|---|---|---|
| WO | 2016005897 A1 | 1/2016 |
| WO | 2016187718 A1 | 12/2016 |

OTHER PUBLICATIONS

Arumugam, et al., "Use of preoperative gabapentin significantly reduces postoperative opioid consumption: a meta-analysis," Journal of Pain Research, 2016;9:631-640.

Durmus et al., "The post-operative analgesic effects of a combination of gabapentin and paracetamol in patients undergoing abdominal hysterectomy: a randomized clinical trial," Acta Anaesthesiol Scand., Mar. 2007; 51(3):299-304.

Qiu, et al., "Effect of preoperative gabapentin and acetaminophen on opioid consumption in video-assisted thoracoscopic surgery: a retrospective study," Romanian Journal of Anaesthesia and Intensive Care, 2018;25(1):43-48.

Seib, et al., "Preoperative gabapentin for postoperative analgesia: a meta-analysis," Can J Anaesth., May 2006; 53(5):461-9.

Chiriac et al., "The influence of excipients on physical and pharmaceutical properties of oral lyophilisates containing a pregabalin-acetaminophen combination," Expert Opinion on Drug Delivery, 2017; 14(5):589-599.

Kamble et al., "Fabrication and Evaluation of Bilayer Floating Tablet Containing Conventional Ibuprofen and Modified Release Pregabalin for Combination Pharmacotherapy of Neuropathic Pain," Asian Journal of Pharmaceutics, Jul.-Sep. 2016 (Suppl); 10(3):S290-S299.

Olmedo-Gaya, et al., "Oral pregabalin for postoperative pain relief after third molar extraction: a randomized controlled clinical trial," Clin. Oral Invest., 2016; 20:1819-1826.

Rafiq et al., "Multimodal analgesia versus traditional opiate based analgesia after cardiac surgery, a randomized controlled trial," Journal of Cardiothoracic Surgery, 2014; 9(52); 8 pgs.

* cited by examiner

IR + SR

| Pregabalin | Acetaminophen |
|---|---|
| 25 mg | 650 mg |
| 37.5 mg | 650 mg |
| 50 mg | 650 mg |

- Pre-Op Formulation
- Pregabalin will be released immediately
- Acetaminophen will be sustained released over the duration of 8 hrs.
- Two tablets taken three times a day.

SR + SR

| Pregabalin | Acetaminophen |
|---|---|
| 25 mg | 650 mg |
| 37.5 mg | 650 mg |
| 50 mg | 650 mg |

- Pre-Op Formulation
- Acetaminophen and Pregabalin will be sustained released over the duration of 8 hrs.
- Two tablets taken three times a day.

IR + IR

| Pregabalin | Acetaminophen |
|---|---|
| 12.5 mg | 500 mg |
| 25 mg | 500 mg |
| 37.5 mg | 500 mg |

- Pre-Op Formulation
- Acetaminophen and Pregabalin will be released immediately.
- Two tablets taken four times a day.

FIG. 1

FIXED DOSE COMBINATION FORMULATIONS FOR TREATING PAIN

This application claims priority to our copending U.S. provisional application with the Ser. No. 62/564,699, which was filed Sep. 28, 2017.

FIELD OF THE INVENTION

The field of the invention is compositions and methods for combination formulations for treating pain, especially as it relates to combinations of non-steroidal analgesics (NSAID) with gamma-amino butyric acid (GABA) derivatives for oral perioperative administration.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Effective post-operative pain management minimizes discomfort to the patient and has significant psychological advantages. Pain management post-operatively relies primarily on opioid based analgesics. However, patients prescribed opioids post-operatively for prolonged periods of time are at significant risk of developing opioid addiction. Moreover, opioid analgesic therapy is frequently associated with somnolence, respiratory depression, hypotension and bradycardia, nausea and vomiting, pruritus, and constipation. Several non-opioid anti-inflammatory drugs (e.g., acetaminophen, aspirin, ibuprofen, naproxen, ketorolac, diclofenac, meloxicam, celecoxib, mefenamic etc.) have been extensively used to manage pain. However, when administered alone, they are often ineffective at management of certain types of pain. Moreover, administration of many NSAIDs is limited due to their significant adverse effects such as hepatotoxicity, anti-dotting effects, and GI irritation.

To reduce the need for opioid analgesics, multimodal analgesia can be used that takes advantage of different mechanisms of actions within the central and peripheral nervous system. For example, compositions comprising pregabalin and gabapentin in combination with other non-opioid analgesics were described in multimodal analgesia. Gabapentin and pregabalin are structural analogues of neurotransmitter gamma-aminobutyric acid but rather than being functionally related, they bind to the α-2-δ subunit of voltage gated calcium channels. By blocking these channels, pregabalin and gabapentin prevent the release of excitatory neurotransmitters and thus prevent central nervous sensitization and as such reduces post-operative opioid dosages (see e.g., *Journal of Pain Research* 2016:9 631-640). However, where gabapentin and acetaminophen were administered pre-operatively, no change in opioid consumption was observed (see e.g., *Rom JAnaesth Intensive Care* 2018; 25: 43-48), possibly due to the saturable L-amino acid transport rendering bioavailability inversely dose-dependent. To circumvent issues associated with bioavailability, injectable formulations comprising gabapentin and acetaminophen were developed as is described in US2017/0290793.

In still other examples, where gabapentin alone was administered pre-operatively, the amount of postoperative opioid analgesics was reduced (see e.g., *Can JAnaesth*. 2006 May; 53(5):461-9). However, pain management with single agent analgesia is frequently less than desirable. Indeed, lower doses of gabapentin and pregabalin were not found effective in pain management while higher doses are associated with side effects, which include dizziness and somnolence. In yet another example, both gabapentin and paracetamol were post-operatively given, which decreased the opioid requirement in these patients (see e.g., *Acta Anaesthesiol Scand*. 2007 March;51(3):299-304). However, pain management with combined post-operative administration is typically accompanied by delayed onset.

Accordingly, there is still a need for oral analgesic formulations that are effective in pain management and that minimize side effects of their components, particularly where the analgesic formulation comprises gabapentin or a derivative of gamma-amino butyric acid and a non-opioid anti-inflammatory drug.

SUMMARY OF THE INVENTION

The inventive subject matter is directed to compositions and methods for fixed-dose combination drugs that are pen-operatively and orally administered, and in which the release of an NSAID (non-steroidal anti-inflammatory drug) and a GABA (gamma- aminobutyric acid)-type calcium channel blocker is performed in a controlled manner to achieve desirable levels of analgesia without precipitation of adverse side effects.

In some embodiments, the NSAID is provided via sustained release pre-operatively to prime an individual with the NSAID such that analgesia is already effective upon termination of anesthesia, while the GABA-type calcium channel blocker is administered pre-operatively in an immediate (typically at lower dose) or sustained (typically at higher dose) release form to reduce central nervous sensitization while minimizing dizziness and nausea. Post-operative administration with immediate release of the NSAID and the GABA-type calcium channel blocker will extend pain relief. Moreover, post-operative sustained release administration of acetaminophen and pregabalin can also be used to reduce dosing frequency of one or both drugs.

Thus, in one aspect of the inventive subject matter, the inventors contemplate fixed-dose combination drug that include an NSAID (non-steroidal anti-inflammatory drug) as a first drug component, and a GABA (gamma- aminobutyric acid)-type calcium channel blocker as a second drug component. In preferred aspects, the fixed-dose combination drug is formulated for oral administration, wherein the fixed-dose combination drug is formulated to provide upon oral delivery to an individual in need thereof (a) the NSAID in a sustained release and the GABA-type calcium channel blocker in an immediate release; (b) the NSAID in a sustained release and the GABA-type calcium channel blocker in a sustained release; or (c) the NSAID in an immediate release and the GABA-type calcium channel blocker in an immediate release.

In especially preferred aspects, and as used herein, the term "NSAID" refers to various non-opioid analgesic compounds and especially includes acetaminophen, acetyl salicylic acid, ibuprofen, naproxen, ketoprofen, diclofenac, piroxicam, phenylbutazone, mefenamic acid, and celecoxib, and more preferably acetaminophen or ibuprofen. It is also preferred that the GABA (gamma- aminobutyric acid)-type calcium channel blocker is an anti-epileptic compound, and more preferably pregabalin or gabapentin. Therefore, in some embodiments, the NSAID is acetaminophen or ibuprofen and the GABA (gamma-aminobutyric acid)-type calcium channel blocker is pregabalin or gabapentin (e.g., NSAID is acetaminophen and the GABA (gamma-aminobutyric acid)-type calcium channel blocker is pregabalin).

In further embodiments, the fixed-dose combination drug is formulated to provide upon oral delivery to the individual in need thereof the NSAID in the sustained release and the GABA-type calcium channel blocker in the immediate release, while in other embodiments the fixed-dose combination drug is formulated to provide upon oral delivery to the individual in need thereof the NSAID in the sustained release and the GABA-type calcium channel blocker in the sustained release, and in still other embodiments the fixed-dose combination drug is formulated to provide upon oral delivery to the individual in need thereof the NSAID in the immediate release and the GABA-type calcium channel blocker in the immediate release.

Most typically, but not necessarily, the fixed-dose combination drug contains the NSAID in an amount of between 250 mg and 1000 mg per unit dose, or contains the NSAID in an amount of between 400 mg and 700 mg per unit dose. Similarly, contemplated fixed-dose combination drugs may contain the GABA-type calcium channel blocker in an amount of between 5 mg and 600 mg, and more preferably in an amount of between 50 mg and 300 mg per unit dose. Most typically, a unit dose is formulated as tablet or capsule for oral administration. In some embodiments, an individual can take multiple unit doses (e.g., 2-3 tablets) multiple times a day (e.g., two, three, or four times).

It is still further generally contemplated that in the fixed-dose combination drugs presented herein cumulatively between 40-80% of the NSAID in the sustained release is released over a period of 6-8 hours, and or cumulatively between 40-80% of the GABA-type calcium channel blocker in the sustained release is released over a period of 2 hours. On the other hand, it is contemplated that cumulatively at least 80% of the NSAID in the immediate release is released over a period of 30 minutes and that cumulatively at least 80% of the GABA-type calcium channel blocker in the immediate release is released over a period of 30 minutes.

In another aspect of the inventive subject matter, the inventors contemplate a fixed-dose combination drug kit that includes a pre-op fixed-dose combination drug and a post-op fixed-dose combination drug. Most typically, each of the pre-op and post-op fixed-dose combination drugs are formulated for oral administration, and each of the pre-op and post-op fixed-dose combination drugs comprise an NSAID (non-steroidal anti-inflammatory drug) as a first drug component, and a GABA (gamma- aminobutyric acid)-type calcium channel blocker as a second drug component. Moreover, it is contemplated that the pre-op fixed-dose combination drug is formulated to provide upon oral delivery to an individual in need thereof the NSAID in a sustained release and the GABA-type calcium channel blocker in an immediate release, or is formulated to provide upon oral delivery to the individual in need thereof the NSAID in a sustained release and the GABA-type calcium channel blocker in a sustained release. The post-op fixed-dose combination drug is formulated to provide upon oral delivery to an individual in need thereof the NSAID in an immediate release and the GABA-type calcium channel blocker in an immediate release.

Consequently, the inventors also contemplate a method of delivering analgesic agents to an individual in need thereof. Such methods will advantageously provide analgesia (treat pain), and will reduce nausea, emesis, and/or anxiety. Especially contemplated methods will include a step of pre-operatively administering to the individual a pre-op fixed-dose combination drug via oral route, and a further step of post-operatively administering to the individual a post-op fixed-dose combination drug via oral route. Most typically, each of the pre-op and post-op fixed-dose combination drugs are formulated for oral administration, and each of the pre-op and post-op fixed-dose combination drugs comprise an NSAID (non-steroidal anti-inflammatory drug) as a first drug component, and a GABA (gamma-aminobutyric acid)-type calcium channel blocker as a second drug component. This oral dosage form may encompass multiple forms including a solid, gel, liquid, dissolvable wafer, or any other form suitable for oral administration. It is still further preferred that the pre-op fixed-dose combination drug is formulated to provide upon oral delivery to an individual in need thereof the NSAID in a sustained release and the GABA-type calcium channel blocker in an immediate release or the NSAID in a sustained release and the GABA-type calcium channel blocker in a sustained release. The post-op fixed-dose combination drug is preferably formulated to provide upon oral delivery to an individual in need thereof the NSAID in an immediate release and the GABA-type calcium channel blocker in an immediate release. With respect to the NSAID, the GABA (gamma- aminobutyric acid)-type calcium channel blocker, and formulations thereof, the same considerations as provided above apply.

In still further contemplated aspects, the inventors also contemplate a method of delivering analgesic agents to an individual in need thereof. Such methods will include a step of pre-operatively administering to the individual an NSAID (non-steroidal anti-inflammatory drug) and a GABA (gamma- aminobutyric acid)-type calcium channel blocker. Most typically, the NSAID (non-steroidal anti-inflammatory drug) for pre-op administration is formulated for sustained release upon oral delivery to the individual, and the GABA (gamma- aminobutyric acid)-type calcium channel blocker for pre-op administration is formulated for immediate or sustained release upon oral delivery to the individual. In another step, an NSAID (non-steroidal anti-inflammatory drug) and a GABA (gamma-aminobutyric acid)-type calcium channel blocker are post-operatively administered to the individual, wherein the NSAID (non-steroidal anti-inflammatory drug) and the GABA (gamma-aminobutyric acid)-type calcium channel blocker for post-op administration are each formulated for immediate release upon oral delivery to the individual. As before, with respect to the NSAID, the GABA (gamma- aminobutyric acid)-type calcium channel blocker, and formulations thereof, the same considerations as provided above apply.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1 depicts Tables with exemplary compositions for fixed-dose combination drugs.

DETAILED DESCRIPTION

Figure 2:
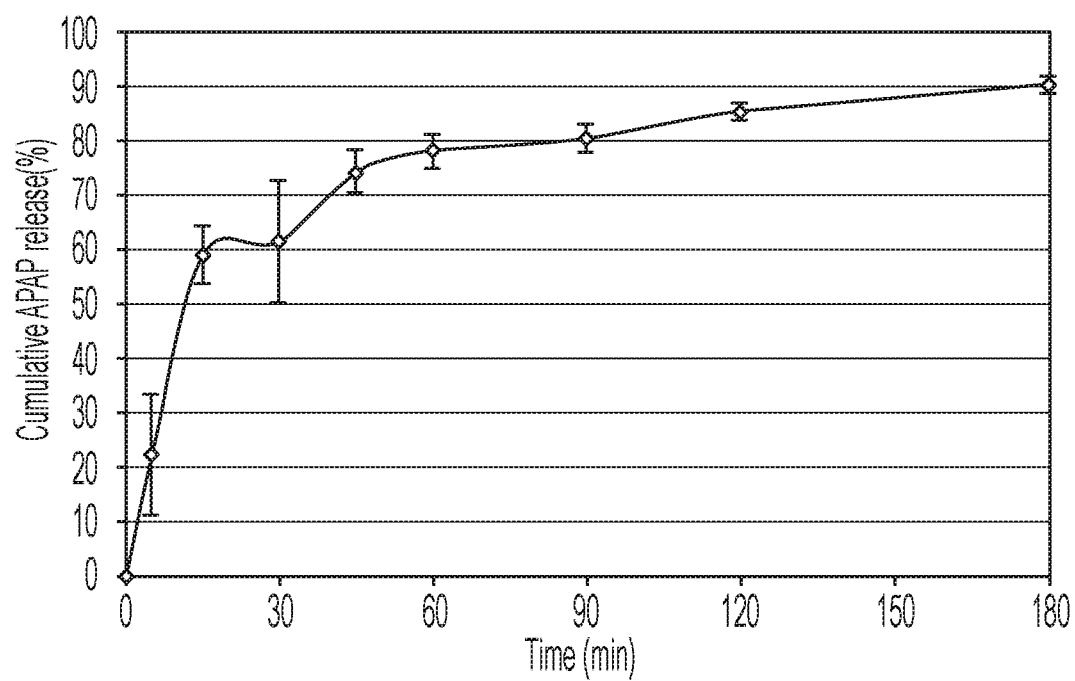
FIG. 2 depicts dissolution profiles of APAP-IR Caplets in water without SSG.

The inventors have discovered that analgesic compositions comprising an NSAID and a GABA-type calcium channel blocker can be orally administered in a manner that not only reduces the need for opioid medication, but also in a manner that reduces adverse side effects of the GABA-type calcium channel blocker while optimizing NSAID administration at levels that are deemed clinically safe.

More particularly, the inventors contemplate that the NSAID and the GABA-type calcium channel blocker can be formulated into a single fixed-dose combination drug such that the release of the NSAID and the GABA-type calcium channel blocker can be performed in a controlled manner to optimize analgesic effect. Most commonly, pregabalin (a GABA-type calcium channel blocker) is pre-operatively and orally administered in a single capsule to reduce central nervous sensitization, while acetaminophen (an NSAID) is post-operatively and intravenously administered over multiple dosages. Unfortunately, pregabalin often leads to dizziness, drowsiness, and nausea, especially at higher dosages, while acetaminophen has a relatively short half-life in vivo and as such requires frequent administration. To compound such difficulties, administration of acetaminophen is typically limited to 4 g/day due to its hepatotoxicity at higher dosages. As such, acetaminophen is typically not administered pre-operatively.

In contrast, the inventors now contemplate that where the NSAID and the GABA-type calcium channel blocker are formulated into a single fixed-dose combination drug with distinct release characteristics, such drug combination can be administered peri-operatively (i.e., pre- and post-operatively, typically with different release characteristics) such that side effects of the GABA-type calcium channel blocker are minimized and the analgesic effect of the NSAID is maximized. For example, contemplated fixed-dose combination drug may thus comprise an NSAID as a first drug component, and a GABA-type calcium channel blocker as a second drug component, wherein the fixed-dose combination drug(s) is/are formulated for oral administration. This oral dosage form may encompass multiple forms including a solid, gel, liquid, dissolvable wafer, or any other form suitable for oral administration.

In one aspect of the inventive subject matter, a fixed-dose combination drug for pre-operative administration is formulated to provide upon oral delivery to an individual in need thereof the NSAID in a sustained release and the GABA-type calcium channel blocker in an immediate release, or the NSAID in a sustained release and the GABA-type calcium channel blocker in a sustained release. Such fixed-dose combination drugs will advantageously provide a delayed onset of analgesia via the NSAID while immediately providing a reduction of central nervous sensitization via the GABA-type calcium channel blocker at lower doses (e.g., equal or less than 25 mg/dose) via immediate release, or a gradual reduction of central nervous sensitization via the GABA-type calcium channel blocker at higher doses (e.g., more than 25 mg/dose) via sustained release.

In another aspect of the inventive subject matter, a fixed-dose combination drug for post-operative administration is formulated to provide upon oral delivery to an individual in need thereof the NSAID and the GABA-type calcium channel blocker in an immediate release at a desired or required dosage.

For example, two capsules of a fixed-dose combination drug with the GABA-type calcium channel blocker at lower doses (e.g., equal or less than 25 mg/dose) and the NSAID at a higher dose (e.g., 650 mg/dose) may be given pre-operatively (e.g., within 4 hours) where the GABA-type calcium channel blocker is in an immediate release formulation and the NSAID is in a sustained release form. On the other hand, two capsules of a fixed-dose combination drug with the GABA-type calcium channel blocker at higher doses (e.g., more than 25 mg/dose) and the NSAID at a higher dose (e.g., 650 mg/dose) may be given pre-operatively (e.g., within 8 hours) where the GABA-type calcium channel blocker and the NSAID are in a sustained release form. Additional capsules of a fixed-dose combination drug with the GABA-type calcium channel blocker at lower doses (e.g., equal or less than 25 mg/dose) and the NSAID at a regular dose (e.g., 500 mg/dose) may be given post-operatively with both drugs in an immediate release formulation. Of course, it should also be appreciated that all oral dosage formulations and modes/schedules of oral administration can also be combined with parenteral administration (especially i. v. administration of the NSAID and/or the GABA-type calcium channel blocker).

With respect to the release kinetics, it is generally preferred that where the drug is formulated for immediate release from the fixed-dose combination drug, at least 80% of the drug is cumulatively released within 30 minutes. On the other hand, where the drug is formulated for sustained release from the fixed-dose combination drug, between 40-80% of the GABA-type calcium channel blocker in the sustained release is released over a period of 2 hours or between 40-80% of the NSAID in the sustained release is released over a period of 6-8 hours.

Of course, it should be appreciated that the particular formulation and release kinetics need not be limited to the above examples, but will indeed include fixed-dose combination drugs that are formulated to (i) release the NSAID via immediate release and the GABA-type calcium channel blocker via immediate release, (ii) release the NSAID via immediate release and the GABA-type calcium channel blocker via sustained release, (iii) release the NSAID via sustained release and the GABA-type calcium channel blocker via immediate release, and (iv) release the NSAID via sustained release and the GABA-type calcium channel blocker via sustained release. There are numerous manners of controlling release of a drug from a fixed-dose combination drug known in the art, and all of those are deemed suitable for use herein. Thus, drug release may be performed using ion exchange, erosion or biodegradation, or via release from a compacted form or layer as is discussed in more detail below.

Moreover, it should be appreciated that particularly preferred fixed-dose combination drugs are formulations for contemporaneous oral administration of both drugs. As is shown in more detail below, such formulations will have two or more layers or other components that are designed to achieve the specific release character for the particular drug component. Viewed from a different perspective, the NSAID and GABA-type calcium channel blocker are preferably in the same dosage unit. However, in further contemplated aspects, the NSAID and the GABA-type calcium channel blocker may also be administered as separate dosage units, each with their own distinct release characteristics.

Of course, it should be appreciated that the exact amount of the NSAID and GABA-type calcium channel blocker may vary considerably, and the particular quantity will at least in part depend on the particular drug, the type of release, and the patient age or condition. However, it is generally preferred that the quantities of the NSAID and GABA-type calcium channel blocker will generally be within the range of administration known in the art. Thus, the amount of the NSAID will typically be within the range of 10-4000 mg per dosage unit (e.g., capsule or tablet), or between 250 mg and 1000 mg, and more typically between 100-1000 mg per dosage unit, and most typically between 400 mg and 700 mg. For example, suitable NSAID quantities may be between 100-200 mg, or between 200-400 mg, or between 400-650 mg, or between 650-900 mg, or between 900-1300 mg, or even higher. Likewise, suitable quantities for the GABA-type calcium channel blocker may be between 5 mg and 100 mg per dosage unit (e.g., capsule or tablet), or between 10- 50 mg, or between 1-10 mg, or between 10-20 mg, or between 20-50 mg, or between 50-100 mg, or between 100-2000 mg, or between 5-600 mg, or between 10-600 mg, or even higher. Viewed from a different perspective, the usual daily (i.e., 24 hour time period) dose may depend on the specific compound, method of treatment and condition treated. Therefore, contemplated daily doses for the GABA-type calcium channel blocker (e.g., gabapentin or derivative of gamma-amino butyric acid) will be about 25 to 1000 mg, and 50 to 5000 mg of non-opioid analgesic (e.g., NSAID).

Most typically, but not necessarily, the quantity for the NSAID will be equal or more than 500 mg, or equal or more than 600 mg, or equal or more than 700 mg, or equal or more than 800 mg where the NSAID is formulated for sustained release. Conversely, the quantity for the NSAID will be equal or less than 500 mg, or equal or less than 400 mg, or equal or less than 300 mg where the NSAID is formulated for immediate release. Likewise, the quantity for the GABA-type calcium channel blocker will be equal or more than 25 mg, or equal or more than 37 mg, or equal or more than 50 mg, or equal or more than 100 mg, or equal to or more than 200, or equal to or more than 300, or equal to or more than 600 where the GABA-type calcium channel blocker is formulated for sustained release. Conversely, the quantity for the GABA-type calcium channel blocker will be equal or less than 25 mg, or equal or less than 13 mg, or equal or less than 600 mg where the GABA-type calcium channel blocker is formulated for immediate release.

As will be readily appreciated, such specific release characteristics will allow tailoring analgesic effect over a wide range, which will advantageously allow reduction of undesired side effects. For example, smaller quantities (e.g., 25 mg or less) of the GABA-type calcium channel blocker may be orally administered in an immediate release form or higher quantities (e.g., more than 25 mg) in a sustained release form to reduce pre-operative nausea and/or dizziness and to reduce central nervous sensitization, while at the same time higher quantities of the NSAID may be pre-operatively administered in a sustained form to thereby initiate and maintain analgesia such that the patient has the benefit of analgesia upon the termination of anesthesia. Once anesthesia is concluded, formulations for immediate release of both drugs may then be administered, preferably from a single fixed-dose combination drug.

Therefore, in another aspect of the inventive subject matter, the inventors contemplate a fixed-dose combination drug kit that includes a pre-op fixed-dose combination drug and a post-op fixed-dose combination drug, wherein each of the pre-op and post-op fixed-dose combination drugs comprise an NSAID (non-steroidal anti-inflammatory drug) as a first drug component, and a GABA (gamma- aminobutyric acid)-type calcium channel blocker as a second drug component. In such kits, it is generally preferred that the pre-op fixed-dose combination drug is formulated to provide upon oral delivery to an individual in need thereof (i) the NSAID in a sustained release and the GABA-type calcium channel blocker in an immediate release, or (ii) the NSAID in a sustained release and the GABA-type calcium channel blocker in a sustained release, and that the post-op fixed-dose combination drug is formulated to provide upon oral delivery to an individual in need thereof the NSAID in an immediate release and the GABA-type calcium channel blocker in an immediate release. With respect to the specific fixed-dose combination drugs, the same considerations as presented herein apply.

Therefore, it should also be recognized that contemplated methods of delivering two or more analgesic agents to an individual in need thereof will include a step of pre-operatively administering to the individual a pre-op fixed-dose combination drug via oral route, and post-operatively administering to the individual a post-op fixed-dose combination drug via oral route. As noted above, each of the pre-op and post-op fixed-dose combination drugs are formulated as described above and are formulated for oral administration. In still other aspects, a method of delivering analgesic agents to an individual in need thereof is contemplated that includes a step of pre-operatively administering to the individual an NSAID (non-steroidal anti-inflammatory drug) and a GABA (gamma- aminobutyric acid)-type calcium channel blocker, wherein the NSAID (non-steroidal anti-inflammatory drug) for pre-op administration is formulated for sustained release upon oral delivery to the individual, and wherein the GABA (gamma-aminobutyric acid)-type calcium channel blocker for pre-op administration is formulated for immediate or sustained release upon oral delivery to the individual. In yet another step, an NSAID (non-steroidal anti-inflammatory drug) and a GABA (gamma-aminobutyric acid)-type calcium channel blocker are post-operatively administered to the individual, wherein the NSAID (non-steroidal anti-inflammatory drug) and the GABA (gamma-aminobutyric acid)-type calcium channel blocker for post-op administration are each formulated for immediate release upon oral delivery to the individual.

Of course, it should be recognized that the nature and type of the NSAID may vary considerably, and among other choices, suitable NSAIDs include acetaminophen, diflunisal, acetyl salicylic acid, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, and celecoxib. However, particularly preferred NSAID compounds include acetaminophen, acetyl salicylic acid, ibuprofen, and naproxen.

Similarly, the nature of the GABA-type calcium channel blocker may vary and it is contemplated that all such blockers are deemed suitable for use herein. Therefore, especially contemplated GABA-type calcium channel blockers include gabapentin, pregabalin, atagabalin, mirogabalin, 4-methylpregabalin, phenibut, and other gabapentinoids (esp. $\alpha_2\delta$-subunit containing VDCCs), and other anticonvulsants drugs.

In addition, contemplated pharmaceutical formulations described herein may comprise one or more of the following: a diluent and a filler, the diluent and filler can be any diluent and a filler suitable for purposes of obtaining properties desirable for an oral dosage form, including, for example, one or more of inorganic diluent, example calcium carbonate and such, cellulose derivative like croscarmellose sodium and such, sugars like lactose such and silicone based for example colloidal silicone dioxide and such, starch and starch deliveries example sodium starch glycolate and such, natural gums example acacia and such. The diluents can be included in any amount suitable for purposes of obtaining properties desirable for an oral dosage form, for example in an amount of about 99.9% to 0%.

The pharmaceutical formulation may further comprise one or more of the following: a compression aid, can be any compression aid suitable for purposes of obtaining properties desirable for an oral dosage form, including, for example (without limitation), one or more of salts of lactose, different grades of mannitol with brand name of Compressol, microcrystalline cellulose with brand name of Avicel, The compression aid can be included in any amount suitable for purposes of obtaining properties desirable for an oral dosage form, for example in an amount of about 99.9% to 0%.

The pharmaceutical formulation may also comprise one or more of the following, a coating agent, can be any coating agent suitable for purposes of obtaining properties desirable for an oral dosage form, including, for example (without limitation), belong to the class of wax, example, carnauba wax, white wax, microcrystalline wax, white wax, yellow wax. Cellulose derivatives such as, cellulose, cellulose acetate, ethyl cellulose, methyl cellulose, cellulose acetate phthalate, hydroxyl ethyl cellulose, hydroxylmethyl cellulose, hydroxyethyl cellulose, hydroxypropyl methyl cellulose, hypermellose, hypermellose phthalate, acrylic polymers such as Eudragit L, Eudragit S, Eudragit L and S, Polylactoide and glycolide derivatives, polypovidone and derivatives, polyvinyl alcohol, polyvinyl acetate, polyvinyl copolymer, gums such as acacia, guar gum, xanthan gum.

The pharmaceutical formulation can also comprise one or more of the following, glidant and lubricant, including, for example (without limitation), magnesium stearate, calcium stearate, stearic acid: hydrogenated vegetable oil (Sterotex, Lubritab, Cutina), mineral oil, polyethylene glycol 4000-6000 (PEG), sodium lauryl sulfate (SLS). The glidant and lubricants can be included in any amount suitable for purposes of obtaining properties desirable for an oral dosage form, for example in an amount of about 50.0% to 0%.

Furthermore, pharmaceutical formulations contemplated herein can comprise pharmaceutically acceptable excipients, for example one or more of buffers, preservatives, and antioxidants, and any pharmaceutically acceptable mixture thereof Additionally, contemplated pharmaceutical formulation can comprise one or more antioxidants suitable for purposes of obtaining properties desirable for an oral dosage forms, including, for example (without limitation), one or more of hydrophobic anti-oxidants, for example butylated hydroxytoluene, butylated hydroxyanisole, propyl gallate, and α-tocopherol, DL-tocopherol, a- tocopherol acetate, Tocopherol polyethylene glycol succinate (Vitamin E TPGS), L-cysteine, or hydrophilic anti-oxidants, including sodium EDTA and thioglycerol. In one embodiment, the concentration of the antioxidants is between 0.005% and 5% w/w of the total formulation. In one embodiment, the one or more antioxidants can improve the stability of the pharmaceutical formulation.

Moreover, it is contemplated that oral dosage forms comprising the pharmaceutical formulations according to the present disclosure can have desirable properties, including desirable stability properties, pharmacokinetic properties, and bioavailability. One skilled in the art can readily determine the stability properties of the present formulations, for example by employing standard testing procedures. For example, stability samples can be assayed for lactam and gabapentin by an HPLC procedure as set forth in *Pharmaceutical Research, Vol. 9, No.5, 1992, Stability Studies of Gabapentin in Aqueous Solutions* by E. Zour, et al., the entire disclosure of which is herein incorporated by reference.

Release kinetics contemplated herein may vary considerably and will at least in part depend on the particular compound (GABA-type calcium channel blocker or the NSAID) in the formulation, or the timing of administration (e.g., pre-op versus post-op). For example, immediate release formulations may be formulated such that cumulatively at least 50%, or at least 60%, or at least 70%, or at least 80%, or at least 90% of the drug (or drugs) is(are)

released within 15 min, or 20 min, or 30 min, or 40 min, or 50 min, or 60 min, or 90 min. Likewise, sustained release formulations may be formulated such that cumulatively at least 50%, or at least 60%, or at least 70%, or at least 80%, or at least 90% of the drug (or drugs) is(are) released within 60 min, or 90 min, or 120 min, or 180 min, or 240 min, or 6 hours, or 8 hours.

For example, in one embodiment, part of the unit dosage form is an immediate release formulation in which the GABA-type calcium channel blocker or the NSAID is released to a cumulative minimum of 75% within 15 min during a standard test procedure (e.g., in vitro dissolution study using USP II dissolution equipment, with 900 mL of dissolution media at pH 3.0, pH 5.5 and pH 6.8, typically following the procedures as outlined in chapter <711> of the USP Dissolution test (see URL: usp.org/sites/default/files/usp/document/harmonization/gen-method/q01_pf_ira_33_4_2007.pdf)).

In another exemplary embodiment, the unit dosage form is an extended release formulation in which either one or both of the drugs are released to a cumulative minimum of 75% within 5 hr during a standard test procedure (e.g., in vitro dissolution study using USP II dissolution equipment, with 900 mL of dissolution media at pH 3.0, pH 5.5 and pH 6.8; supra). In another embodiment, both drugs are released to a cumulative respective minimum of 75% within 8 hr during a standard test procedure (e.g., the in vitro dissolution study using USP II dissolution equipment, with 900 ml of dissolution media at pH 3.0, pH 5.5 and pH 6.8; supra). In another embodiment, both drugs are released to a cumulative respective minimum of 75% within 12 hr during a standard test procedure (e.g., in vitro dissolution study using USP II dissolution equipment, with 900 mL of dissolution media at pH 3.0, pH 5.5 and pH 6.8; supra).

Of course, it should be appreciated that immediate release and sustained release phases in the fixed-dose combination drug may include a single drug (e.g., the GABA-type calcium channel blocker or the NSAID) to provide simultaneous immediate or sustained release of the drug, or that both drugs (GABA-type calcium channel blocker and the NSAID) may be formulated) to provide simultaneous immediate or sustained release of both drugs.

Accordingly, the pharmaceutical formulation according to the present disclosure will be preferably formulated as single unit or multi-unit tablet, powder cachet, capsule, single unit or multi-unit liquid container.

Administration of the oral pharmaceutical formulation according to the present disclosure to a subject occurs during at least one of pre-procedure, intra-procedure, and/or post-procedure. In one embodiment, administration of the oral pharmaceutical formulation is administered to a subject having pain, including pre-procedure, intra-procedure, and/or post-procedural pain. Thus, the pharmaceutical formulations according to the present disclosure are suitable to treat pre-procedure, intra- procedure, and/or post-procedural pain.

The dosage of the present formulations provided to a subject will vary depending upon the active ingredients being administered, the purpose of the administration, such as prophylaxis or therapy, and the state of the subject and/or level of pain, the manner of administration, and the like. In some therapeutic applications, formulations described herein are provided to a subject already suffering from pain, in an amount sufficient to at least partially ameliorate the symptoms of the pain and/or its complications, including, pre-, intra-, and/or post-procedural pain. An amount of present formulations comprising an active ingredient adequate to accomplish this is defined as a "therapeutically effective amount." The dosage to be used in the treatment of a specific case must be subjectively determined by and would be apparent to the ordinarily skilled physician or medical professional. The variables involved for determining a therapeutically effective amount of the present formulations include the specific condition and the size, age, weight, gender, disease penetration, type of procedure, and response pattern of the subject. The compounds can be preferably administered orally.

As noted above, the present formulations can be provided as a unit dose, for example as a tablet, capsule, which taken together comprise a therapeutically effective amount. For example, a unit dose comprising a formulation of the invention can be administered once daily or multiple times daily, for example 1, 2, 3, 4, 5 or 6 times in a 12 or 24 hour period. If multiple unit doses are administered in a given time period, they can be administered at substantially even time intervals. For example, if two unit doses are administered in a 12 hour period, they can be given to the subject 6 hours apart. Multiple unit doses are administered in a given time period can also be administered at substantially uneven time intervals. In one embodiment, a unit dosage form comprises a formulation of the invention in the form of a tablet or capsule for oral administration.

Evaluation of the pharmacokinetics/analgesic properties of contemplated exemplary formulations and other combinations based on the teachings provided herein may be done in primates utilizing a variation of the tail immersion assay (see e.g., *Psychopharmacology* (Berl). 2014; 231(7):1377-1387). Briefly a monkey's tail is injected with carrageenan and immersed in a water bath kept at 42° C. Under these conditions, a normal monkey (control) will not withdraw its tail from the bath, however a monkey treated with carrageenan will rapidly withdraw its tail due to the increased thermal sensitivity associated with the response to the carrageen. Therefore, any increase in time to withdraw its tail correlates with a response to pain. This response will be correlated with blood levels of both the GABA-type calcium channel blocker and the NSAID.

As noted above, it should also be appreciated that the fixed-dose combination drugs presented herein may also be employed to treat or reduce nausea, vomiting, dizziness, and/or anxiety in an individual. Most typically, such methods will use oral administration of the fixed-dose combination drugs, preferably in a solid form such as a tablet or capsule. As will be appreciated, administration and schedule is typically dependent on the condition of the individual as well as the age, and possibly disease state. However, in most typical aspects, the individual will receive between one and four dosage units of the fixed-dose combination drug per day, preferably in equal intervals where more than one dosage unit is delivered to the individual.

Therefore, typical total daily dosages for such use will be between 100-4000 mg of the NSAID and between 10-600 mg of the GABA-type calcium channel blocker. For example, suitable total daily dosages will be between 200-600 mg, or between 600-1200 mg, or between 1200-2400 mg, or between 2400-4000 mg of the NSAID, and between 10-60 mg, or between 60-120 mg, or between 120-240 mg, or between 240-600 mg of the GABA-type calcium channel blocker. Viewed from a different perspective, contemplated dosage units will include those as described for analgesia above.

Exemplary Formulations and Results

In general, it should be appreciated that drug combinations can be prepared with and without specific time release characteristics. While specific time release characteristics for at least one drug are generally preferred, the initial examples in Tables 1-4 below show selected embodiments using no specific time release characteristics.

TABLE 1

| Composition | Capsule 1 Quantity (mg) | Capsule 2 Quantity (mg) |
|---|---|---|
| Acetaminophen | 500 | — |
| Gabapentin | 100 | 200 |
| Lactose | 95 | 50 |
| Mg. Stearate | 5 | 2.5 |

TABLE 2

| Composition | Capsule 1 Quantity (mg) | Capsule 2 Quantity (mg) |
|---|---|---|
| Acetaminophen | 500 | — |
| Pregabalin | 50 | 50 |
| Lactose | 95 | 50 |
| Mg. Stearate | 5 | 2.5 |

TABLE 3

| Composition | Capsule 1 Quantity (mg) | Capsule 2 Quantity (mg) |
|---|---|---|
| Acetaminophen | 500 | — |
| Gabapentin | 100 | 200 |
| Lactose | 95 | 50 |
| Mg. Stearate | 5 | 2.5 |

TABLE 4

| Composition | Capsule 1 Quantity (mg) | Capsule 2 Quantity (mg) |
|---|---|---|
| Acetaminophen | 500 | — |
| Pregabalin | 100 | 200 |
| Lactose | 95 | 50 |
| Mg. Stearate | 5 | 2.5 |

The above capsule compositions of Tables 1-3 were made using the following exemplary protocols: Acetaminophen and gabapentin or pregabalin were blended along with lactose. The lubricant, magnesium stearate, was added to the above mixture and blended. The resulting powder was filled in an enteric coated capsule. Separately, pregabalin was blended with lactose and magnesium and filled in a hard-shell gelatin capsule. One enteric coated capsule can be administered along with one immediate release hard gelatin capsule. The capsules maybe further packaged in a plastic container. Alternatively, tables can be made as follows: Acetaminophen and gabapentin were blended with lactose and magnesium stearate and sprayed on MCC beads. The beads were further coated with a solution of Eudragit L 100, talc and triethyl citrate. Separately Gabapentin was sprayed on MCC beads. The coated and uncoated beads were filled in capsules. The capsules may be further packaged in a plastic container.

The capsule compositions of Table 4 can be prepared as follows: acetaminophen and gabapentin or pregabalin and hydroxypropyl methyl cellulose were blended along with lactose. The lubricant (magnesium stearate) was added to the above mixture and blended. The resulting powder was compressed on a single press punch tableting machine. The resulting tablet was again compressed further with pregabalin/gabapentin blended with lactose and magnesium stearate. The capsules maybe further packaged in a plastic container.

Compositions and formulations for specific release characteristics: The following provides exemplary guidance for the preparation of formulations with one or more specific release characteristics suitable for use herein.

Immediate and Sustained Release Formulations: The following examples were made to demonstrate that drugs presented herein can be released with desired release characteristics with release of a significant portion of the drug (e.g., 80% cumulatively) from few minutes to several hours.

For these examples, caplets were prepared and each 1150 mg of Caplet contained 500 mg of acetaminophen (APAP), along with diluent, magnesium stearate and talc as lubricants, and HPMC (Methocel ES; hydroxypropyl methylcellulose) as binder in the quantities shown below in the respective tables. More specifically, APAP and diluent (Avicel PH 101/Avicel PH 102) were mixed using a pestle and mortar with HPMC (5%), wet mass obtained was passed using sieve #18-mesh (1 μm) to prepare the granules. Granules were dried at 400° C. for 30 mins. Later, the dried granules were passed on #60 mesh screen to separate the fines. The weights of the granules (retained on mesh #60) and fines were recorded. Magnesium stearate and talc were mixed to the total mixture to lubricate the granules and fines. Super disintegrant (sodium starch glycolate, SSG) was added to the lubricated mixture (Batch III and IV). Weighted samples were compressed on a rotary tableting machine (Kambert Mini Rotary Ress—8 station) using Natoli 06-124 D#483057; 0.3937×0.7480 CAPSULE SHAPE (Instrumental tablet thickness was adjusted between 2.5 to 3).

Dissolution was measured using a Vankel Dissolution apparatus VK7000, Type: Type II (Paddle), operated at 50 RPM at a temperature of 37.5° C.; Dissolution media was water (freshly collected from Nanopure system); Volume of media: 900 mL. Sampling was done using a Varian VK 8000 autosampler attached to VK7000 dissolution apparatus; Volume of sample withdrawn was 5 mL; was not replenished with fresh medium, but adjusted during the calculations. Line filter was 10 μm filter, and sampling time points were 5, 15, 30, 45, 60, 90, 120, 180 minutes; stored in 2-8° C. until analysis. HPLC analysis followed known protocol using an Agilent 1260 HPLC Infinity attached to autosampler and PDI detector. Data were processed using OpenLab software. Volume of Injection: 10 μL, Wavelength of analysis was 205 nm, Column Temperature: 30° C.; Column used was Thermo Fischer Hypersil Gold aQ 4.6*250 mm, 5 micron size.

Figure 3:
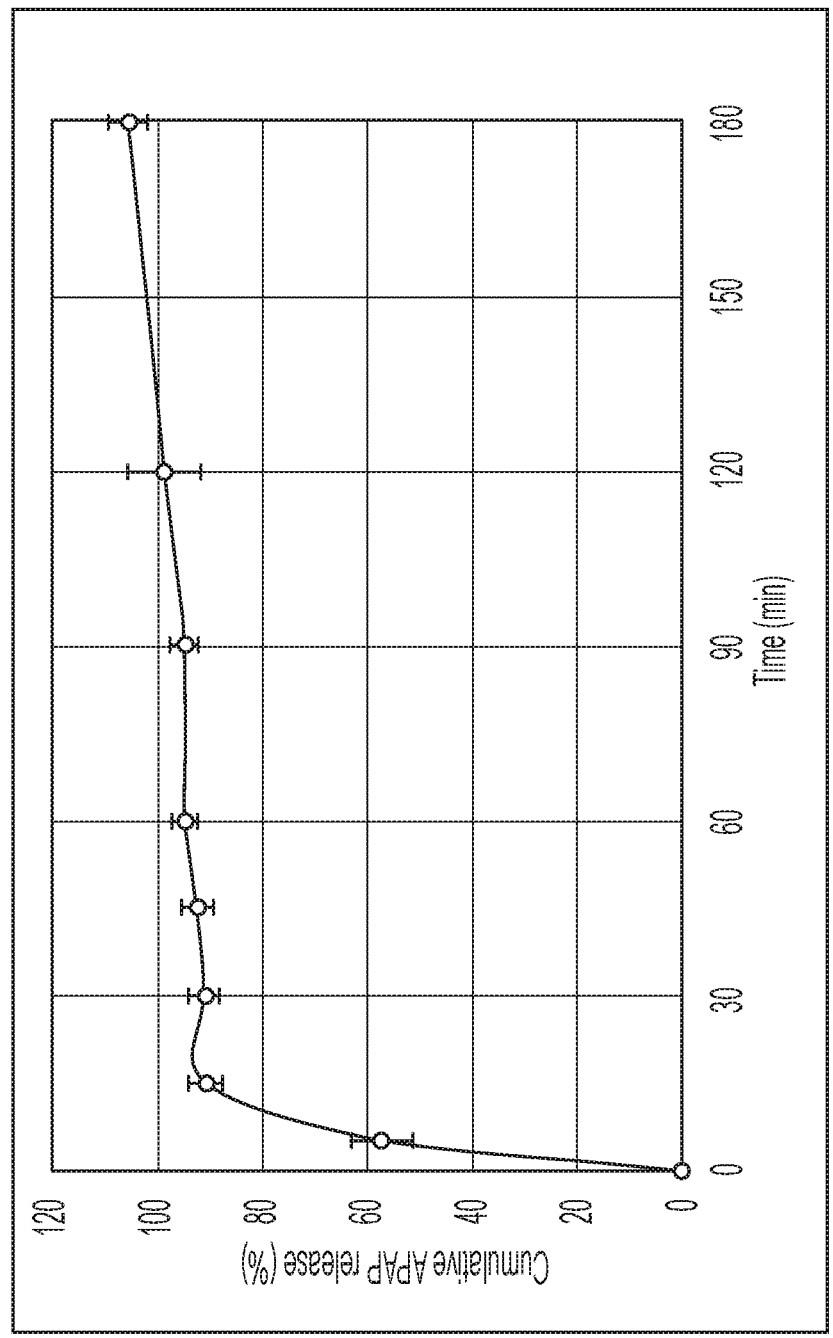
FIG. 3 depicts dissolution profiles of APAP-IR Caplets in water with 2% SSG.
Figure 4:
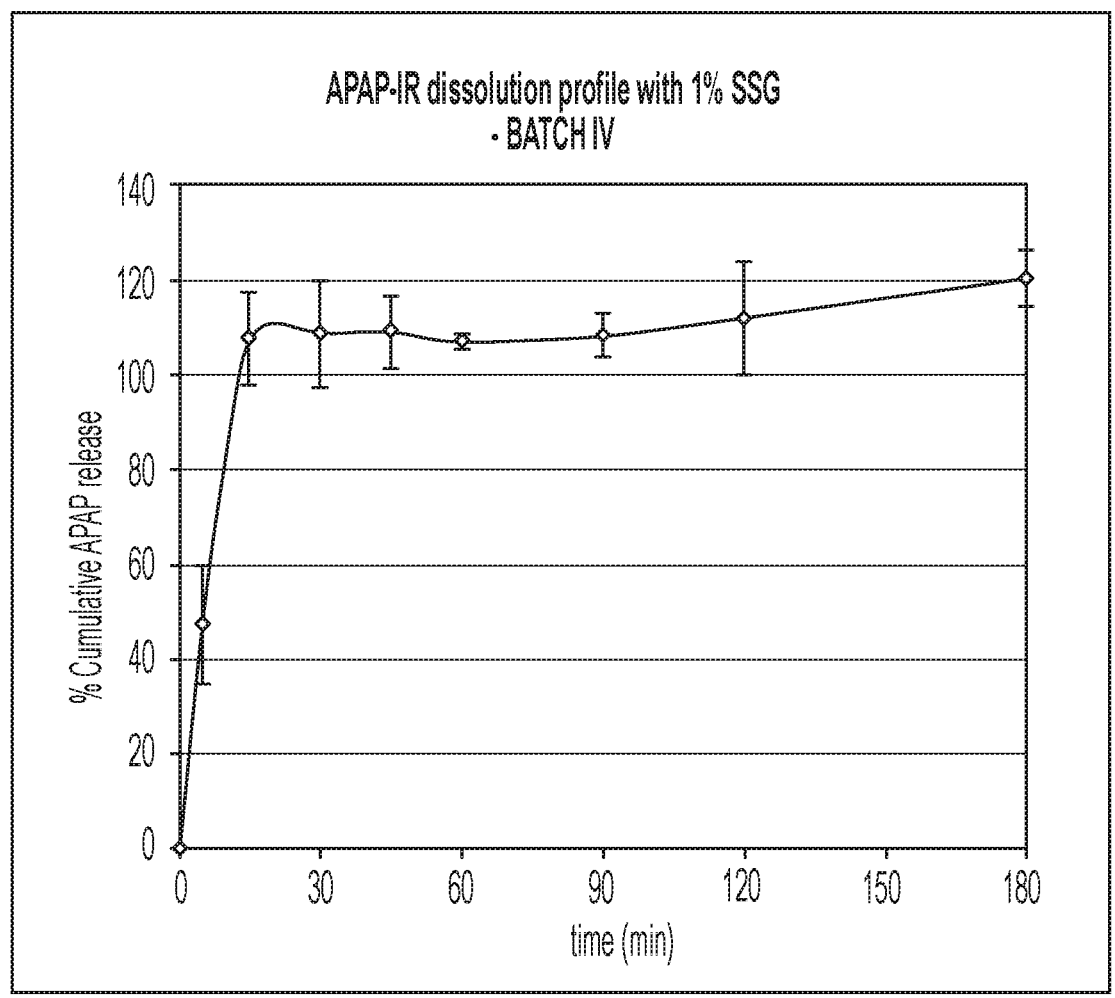
FIG. 4 depicts dissolution profiles of APAP-IR Caplets in water with 1% SSG.

Tables 5-8 depict exemplary formulations used for the release characteristics shown in FIGS. 2-4.

TABLE 5

| Ingredients | Batch I Per tablet |
|---|---|
| Acetaminophen | 500 mg |
| Dicalcium Phosphate Anhydrous | 150 mg |
| Avicel PH 101 | 300 |
| Avicel PH 102 | |
| Talc | 2% |
| Magnesium Stearate | 2% |
| Total Weight (mg) | 1150 |

TABLE 6

| Ingredients | Batch II Per tablet |
| --- | --- |
| Acetaminophen | 500 mg |
| Dicalcium Phosphate Anhydrous | — |
| Avicel PH 101 | — |
| Avicel PH 102 | 650 mg |
| Sodium starch glycolate | — |
| Talc | 248 mg* |
| Magnesium Stearate | 248 mg* |
| Total Weight (mg) | 1150 |

TABLE 7

| Ingredients | Batch III Per tablet |
| --- | --- |
| Acetaminophen | 500 mg |
| Avicel PH 102 | 581 mg |
| Sodium starch glycolate | 23 mg |
| Talc | 23 mg |
| Magnesium Stearate | 23 mg |
| Total Weight (mg) | 1150 |

TABLE 8

| Ingredients | Batch IV Per tablet |
| --- | --- |
| Acetaminophen | 500 mg |
| Avicel PH 102 | 592.5 mg |
| Sodium starch glycolate | 11.5 mg |
| Talc | 23 mg |
| Magnesium Stearate | 23 mg |
| Total Weight (mg) | 1150 |

FIG. 2 depicts the Dissolution Profiles of APAP-IR Caplets in water without SSG (Batch II), FIG. 3 depicts the Dissolution Profiles of APAP-IR Caplets in water with 2% SSG (Batch III), and FIG. 4 depicts the Dissolution Profiles of APAP-IR Caplets in water with 1% SSG (Batch IV). As can be seen from the results, the addition of super-disintegrant (e.g., SSG sodium starch glycolate) increased the release of APAP to so prepared immediate release formulations. Here, more than 80% of APAP was released with the addition of 1% and 2% SSG by 30 mins. 1% SSG was observed to exhibit higher release of APAP in comparison with 2% SSG.

Where delayed release of the drug is desired, release retardants can be used in single as well as bilayer caplets. In this example, Total weight of the caplet was set to be 1150 mg. Of the 1150 mg, the active pharmaceutical ingredients (API) contributed 650 mg (500 APAP+150 PGB (pregabalian) mg), which leaves 450 mg for excipients. In this example, the APAP sustained release layer was assigned 850 mg and the PGB immediate release layer was assigned 300 mg. 5% HPMC (hydroxypropyl methylcellulose) E5 solution in water was used as a binder in the quantities shown in more detail below.

APAP and diluent (Avicel PH 102) were mixed in a mortar and using HPMC (5%), wet mass was passed using sieve #18-mesh (1 um) to prepare the granules. Granules were dried at 400° C. for 30 mins. Later, the dried granules were sieved through #60 mesh screen to separate the fines. The weights of the granules (retained on mesh #60) and fines were recorded. Magnesium stearate and talc were mixed the total mixture to lubricate the granules and fines to provide granules for Layer 1(L1). Pregabalin (PGB) was replaced by placebo. For placebo granules (layer 2, L2), wet mass of Avicel PH102 was prepared using HPMC (5%) and processed in the same way as mentioned above. 850 mg sample (L1) was individually weighed and compressed at thickness (4mm tablet thickness, Kambert Mini Rotary tableting machine 8 station, using Natoli 06-124 D#483057; 0.3937× 0.7480 CAPSULE SHAPE) and the same tablet was pushed in the die. 300 mg placebo granules were placed above the tablet and compressed (3mm tablet thickness) to provide a 1150 mg bilayered caplet. Dissolution, sampling, and HPLC analysis were performed as above, and Tables 9-12 depict exemplary formulations.

TABLE 9

| | Batch BL 1M-P | |
| --- | --- | --- |
| Ingredient | Layer 1 (mg/tab) | Placebo (mg/tab) |
| APAP | 500 | — |
| Avicel PH 102 | 231 | 288 |
| Mg stearate | 17 | 6 |
| Talc | 17 | 6 |
| Methocel K4M HHP | 85 (10%) | — |

TABLE 10

| | Batch BL 1E-P | |
| --- | --- | --- |
| Ingredient | Layer 1 (mg/tab) | Placebo (mg/tab) |
| APAP | 500 | — |
| Avicel PH 102 | 231 | 288 |
| Mg stearate | 17 | 6 |
| Talc | 17 | 6 |
| Ethocel standard 20 | 85 (10%) | — |

TABLE 11

| | Batch BL 7M-P | |
| --- | --- | --- |
| Ingredient | Layer 1 (mg/tab) | Placebo (mg/tab) |
| APAP | 500 | — |
| Avicel PH 102 | 211 | 300 |
| Mg stearate | 17 | 6 |
| Talc | 17 | 6 |
| Methocel K4M HHP | 42.5 (5%) | — |

TABLE 12

| | Batch BL 7E-P | |
| --- | --- | --- |
| Ingredient | Layer 1 (mg/tab) | Placebo (mg/tab) |
| APAP | 500 | — |
| Avicel PH 102 | 211 | 300 |
| Mg stearate | 17 | 6 |
| Talc | 17 | 6 |
| Ethocel standard 20 | 42.5 (5%) | — |

Figure 5:
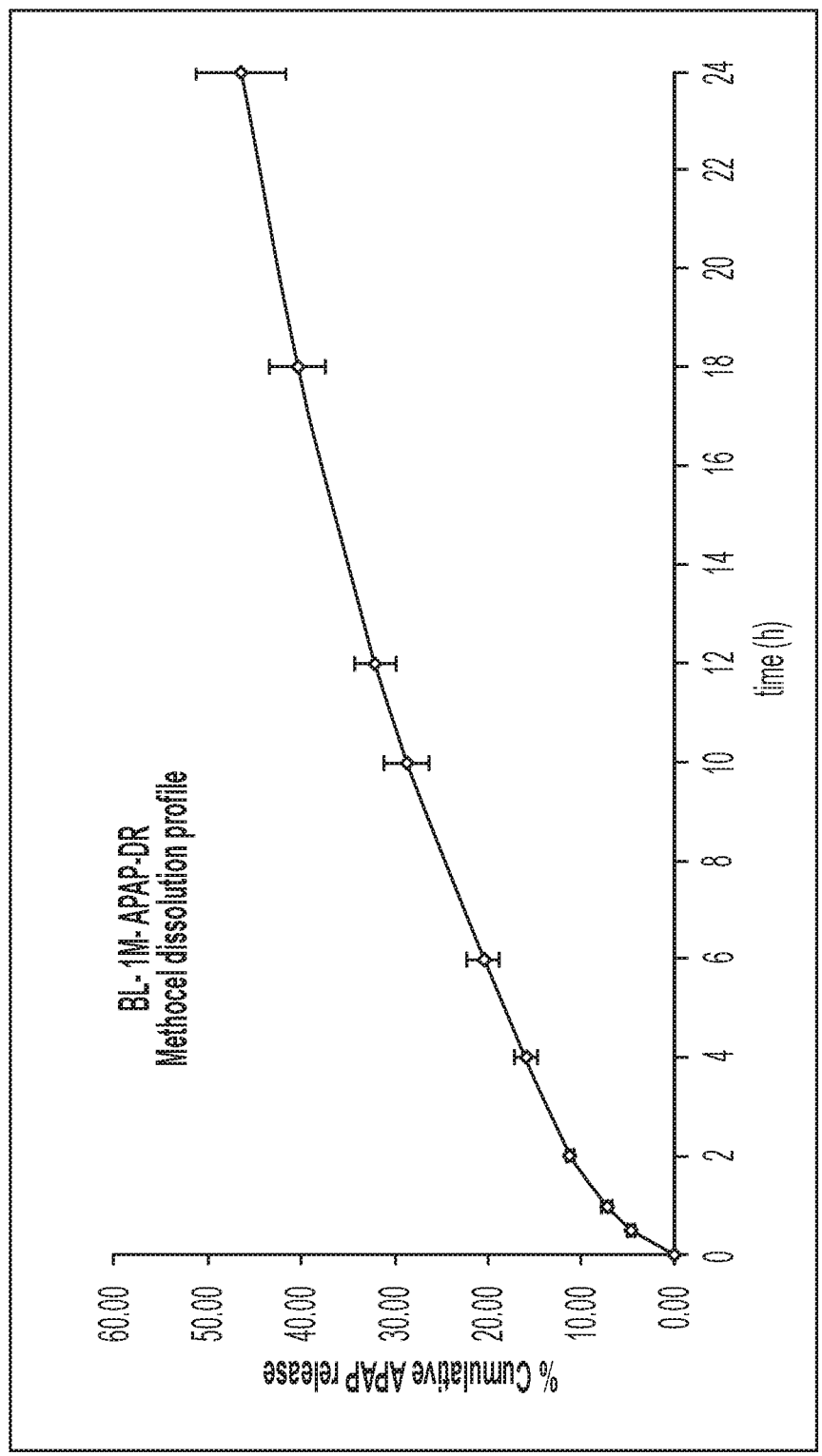
FIG. 5 depicts results for a bilayered caplet containing Acetaminophen (DR) using 10% Methocel in layer 1 and placebo in layer 2.
Figure 6:
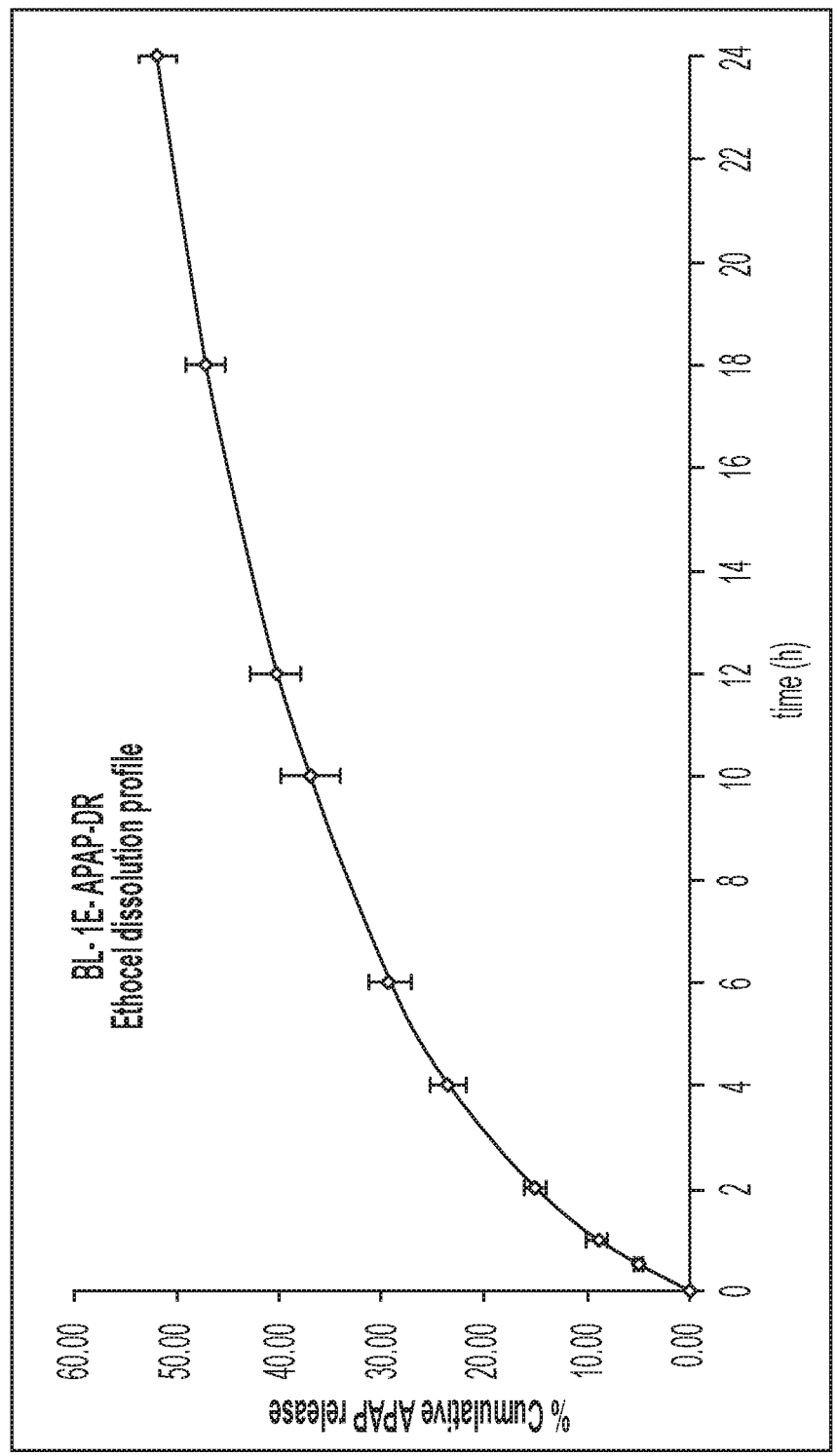
FIG. 6 depicts results for the bilayered caplet containing Acetaminophen (DR) using 10% Ethocel in layer 1 and placebo in layer 2
Figure 7:
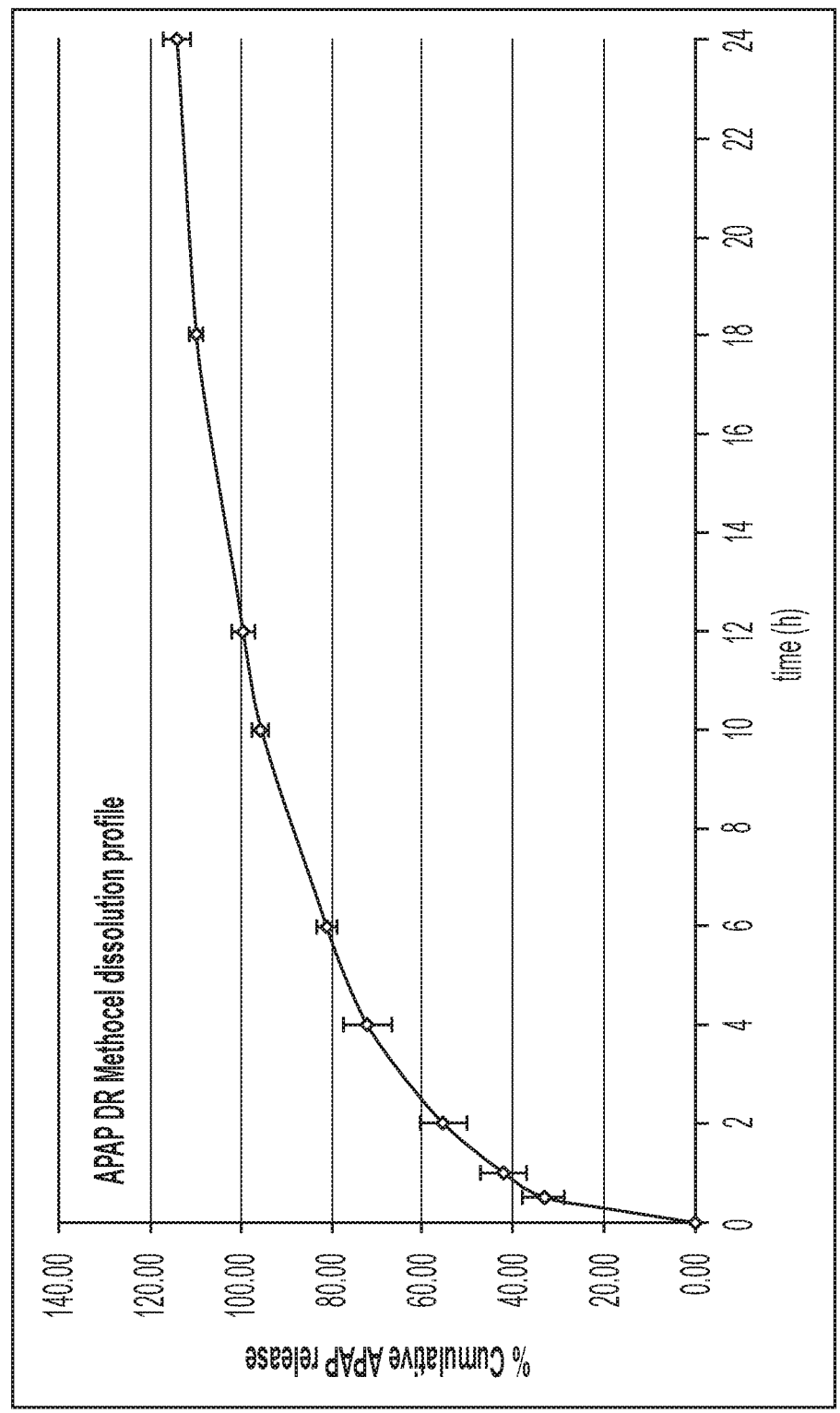
FIG. 7 depicts results for the bilayered Caplet containing Acetaminophen (DR) using 5% Methocel in layer 1 and placebo in layer 2.
Figure 8:
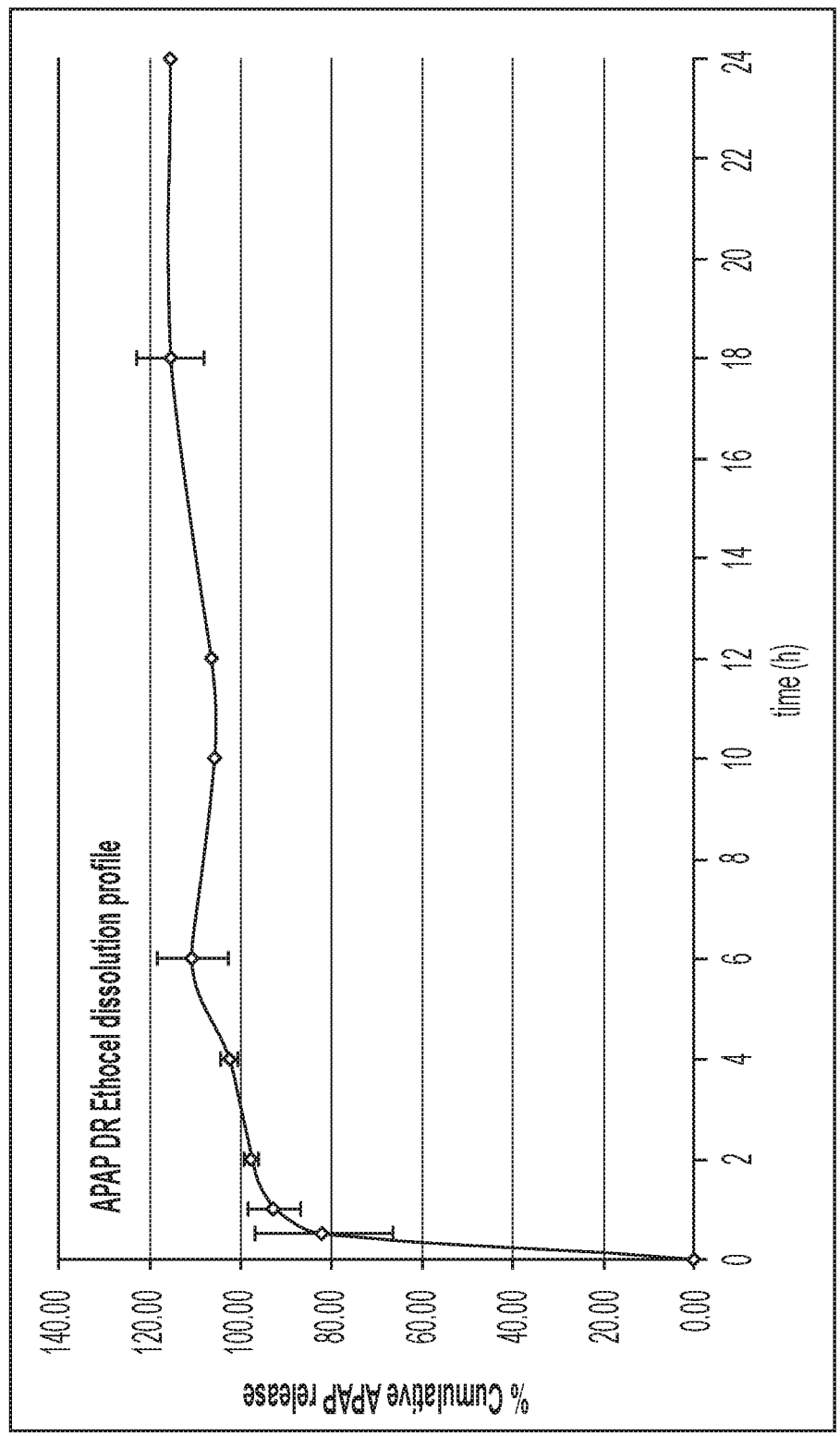
FIG. 8 depicts results for the bilayered caplet containing Acetaminophen (DR) using 5% Ethocel in layer 1 and placebo in layer 2.

FIG. 5 depicts results for a bilayered caplet containing Acetaminophen (DR) using 10% Methocel in layer 1 and placebo in layer 2 (BL-1M-APAP-DR) (n=3 tablet, represented as average±S.D), FIG. 6 depicts results for the bilayered caplet containing Acetaminophen (DR) using 10% Ethocel in layer 1 and placebo in layer 2 (BL-1E-APAP-DR) (n=3 tablet, represented as average±S.D), FIG. 7 depicts results for the bilayered Caplet containing Acetaminophen (DR) using 5% Methocel in layer 1 and placebo in layer 2 (BL-7M- APAP-DR) (n=3 tablet, represented as average±S.D), and FIG. 8 depicts results for the bilayered caplet containing Acetaminophen (DR) using 5% Ethocel in layer 1 and placebo in layer 2 (BL-7E-APAP-DR)(n=3 tablet, represented as average±S.D). As can be seen from the results, release of acetaminophen can be tailored across a wide variety of characteristics, from several minutes to several hours (e.g., for cumulative release of 80%).

Exemplary fixed-dose combination drugs with acetaminophen and pregabalin in a formulation for immediate release of both acetaminophen and pregabalin: The following formulations were prepared as shown in Table 13:

TABLE 13

| Batch No | Pregabalin | Acetaminophen | Layer weight distribution | API Form |
|---|---|---|---|---|
| IRIR 01 | 37.5 mg | 500 mg | L1- APAP-850 mg L2-PGB-300 mg | APAP- granular PGB-Extragranular |
| IRIR 02 | 37.5 mg | 500 mg | L1- APAP-1050 mg L2-PGB-100 mg | APAP- granular PGB-Granular |
| IRIR 03 | 25 mg | 500 mg | L1- APAP-850 mg L2-PGB-300 mg | APAP- granular PGB-Extragranular |
| IRIR 04 | 12.5 mg | 500 mg | L1- APAP-850 mg L2-PGB-300 mg | APAP- granular PGB-Extragranular |

For these formulations, the following general protocol was used to produce the bilayered caplets: APAP and diluent (Avicel PH 102) were mixed in a mortar and using HPMC (5%), wet mass was passed using sieve #18-mesh (1 μm) to prepare the granules. Granules were dried at 400° C. for 30 mins. Later, the dried granules were sieved through #60 mesh screen to separate the fines. The weights of the granules (retained on mesh #60) and fines were recorded. Magnesium stearate and talc were mixed the total mixture to lubricate the granules and fines to provide granules for Layer 1(L1)

PGB was incorporated extragranularly, hence Avicel PH102 granules were prepared initially. placebo granules (layer 2, L2), wet mass of Avicel PH102 was prepared using HPMC (5%) and processed in the same way as mentioned above and the PGB was added to the Avicel granules along with other extragranular materials which included sodium starch glycolate, Magnesium stearate, and Talc.

850 mg sample (L1) was individually weighed and compressed at thickness (3 mm tablet thickness, Kambert Mini Rotary tableting machine 8 station, using Natoli 06-124 D#483057; 0.3937×0.7480 CAPSULE SHAPE) and the same tablet was pushed in the die. 300 mg Layer 2 granules were placed above the tablet and compressed (3 mm tablet thickness) to provide a 1150 mg bilayered caplet, and Tables 14-17 provides exemplary ingredients for the caplets.

TABLE 14

IRIR_APAP_PGB-500/37.5

| Ingredient | Layer I - APAP | LAYER 2 - PGB |
|---|---|---|
| APAP | 500 | |
| PGB | | 37.5 |
| 1% SSG | 8.5 | 3 |
| Mg stearate | 17 | 6 |
| Talc | 17 | 6 |
| HPMC | 17.5 | 8.6 |
| AVICEL 102 | 290 | 238.9 |
| Final weight in layers (mg) | 850 | 300 |
| Total Caplet weight | | 1150 |

TABLE 15

IRIR_APAP_PGB-500/37.5

| Ingredient | Layer I - APAP | LAYER 2 - PGB |
|---|---|---|
| APAP | 500 | |
| PGB | | 37.5 |
| 1% SSG | 10.5 | 1 |
| Mg stearate | 21 | 2 |
| Talc | 21 | 2 |
| HPMC | 17.5 | 2.5 |
| AVICEL 102 | 480 | 55 |
| Final weight in layers (mg) | 1050 | 100 |
| Total Caplet weight | | 1150 |

TABLE 16

IRIR_3_APAP_PGB-500/37.5

| Ingredient | Layer I - APAP | LAYER 2 - PGB |
|---|---|---|
| APAP | 500 | |
| PGB | | 25 |
| 1% SSG | 8.5 | 3 |
| Mg stearate | 17 | 6 |
| Talc | 17 | 6 |
| HPMC | 17.5 | 8.6 |
| AVICEL 102 | 290 | 251.4 |
| Final weight in layers (mg) | 850 | 300 |
| Total Caplet weight | | 1150 |

TABLE 17

IRIR_APAP_PGB-500/12.5

| Ingredient | Layer I - APAP | LAYER 2 - PGB |
|---|---|---|
| APAP | 500 | |
| PGB | | 12.5 |
| 1% SSG | 8.5 | 3 |
| Mg stearate | 17 | 6 |
| Talc | 17 | 6 |
| HPMC | 17.5 | 8.6 |
| AVICEL 102 | 290 | 263.9 |
| Final weight in layers (mg) | 850 | 300 |
| Total Caplet weight | | 1150 |

Figure 9:
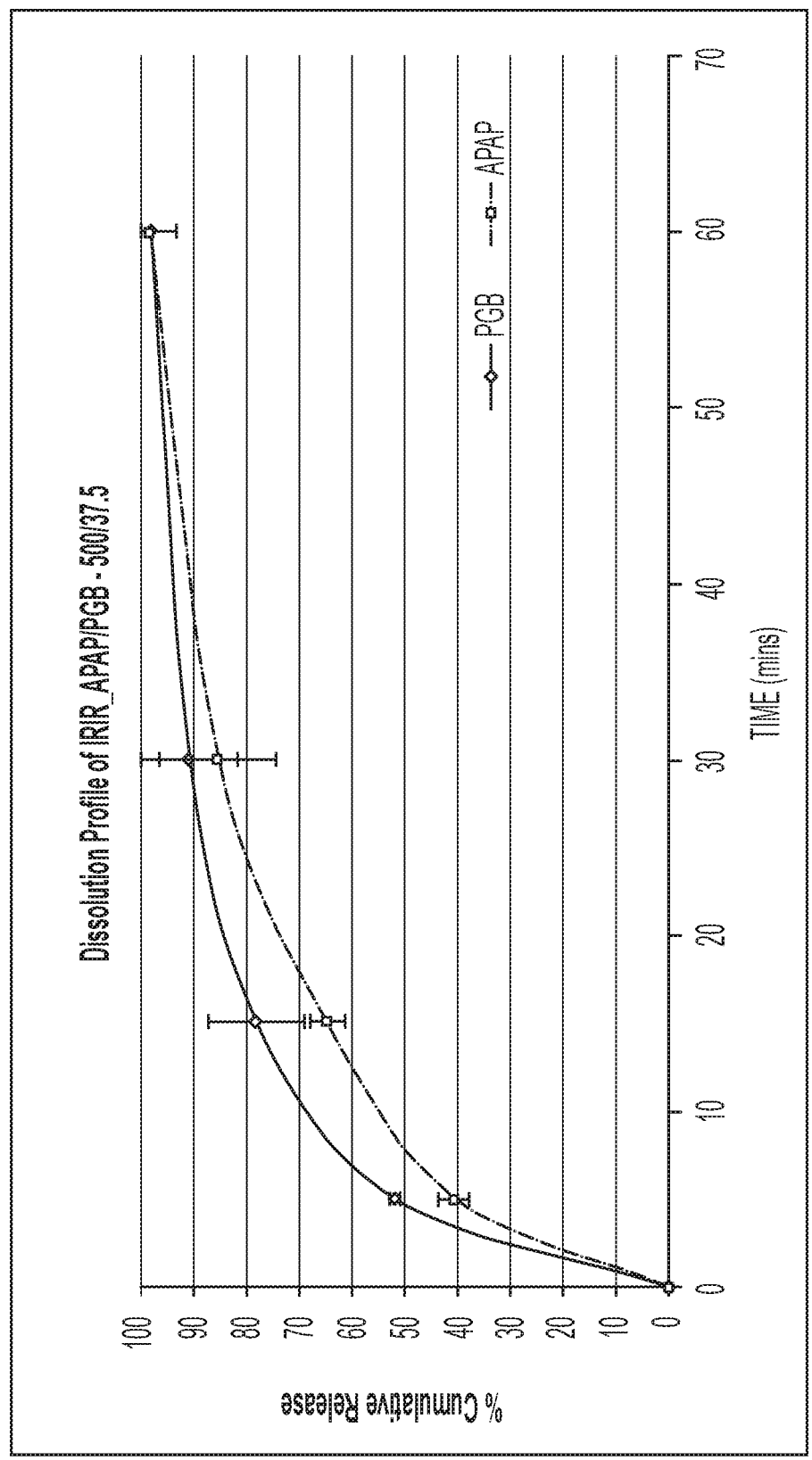
FIG. 9 depicts exemplary results for the release of APAP and PGB from bilayered caplets containing IRIR_APAP-500_PGB-37.5.
Figure 10:
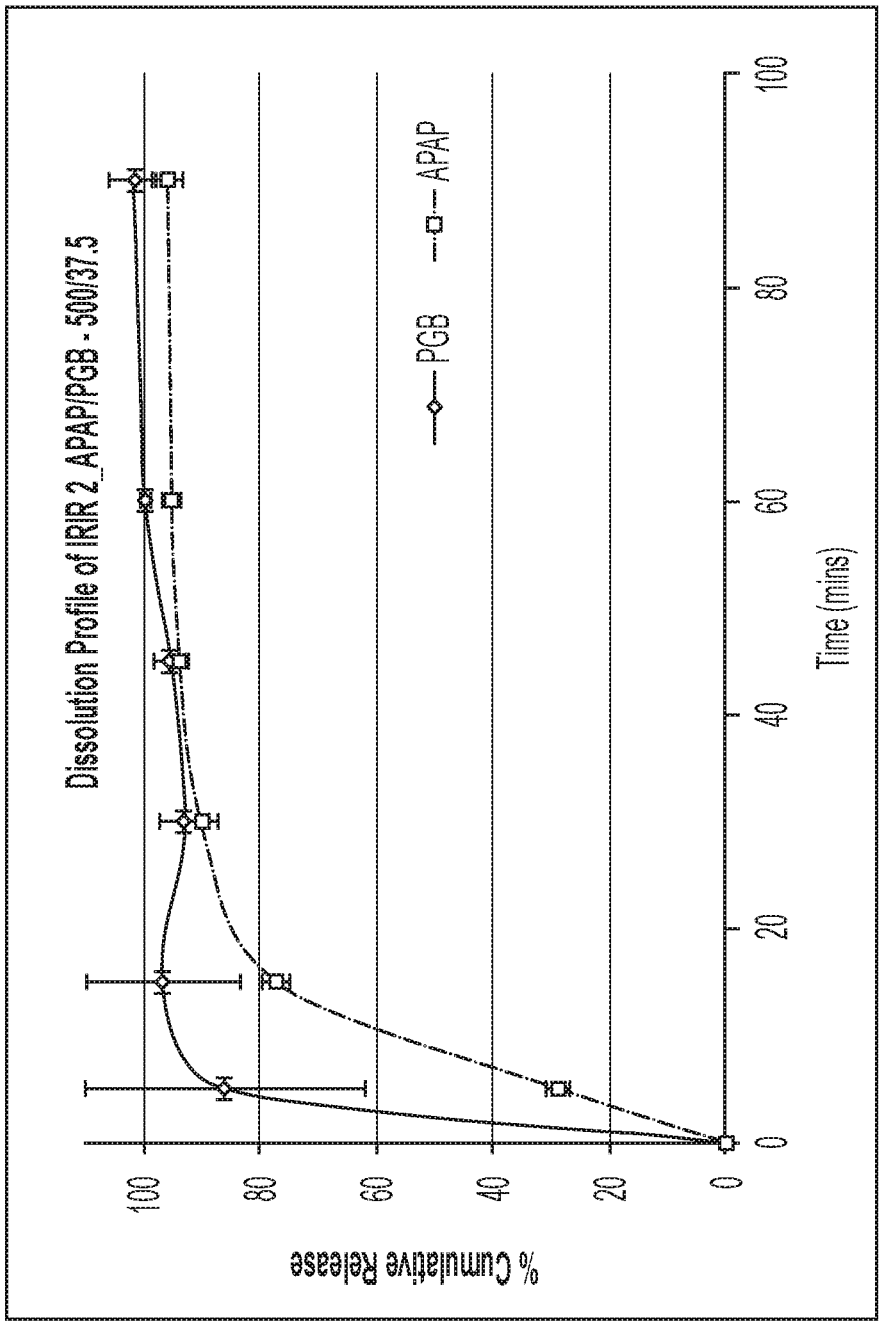
FIG. 10 depicts exemplary results for the release of APAP from Layer 1 of bilayered caplet containing IRIR_APAP-500_PGB-37.5.

FIG. 9 depicts exemplary results for the release of APAP and PGB from bilayered caplets containing IRIR_APAP-500 PGB-37.5 (n=3 tablet, represented as average±S.D), and FIG. 10 depicts exemplary results for the release of APAP from Layer 1 of bilayered caplet containing IRIR_APAP-500 PGB-37.5 (n=3 tablet, represented as average±S.D).

Figure 11:
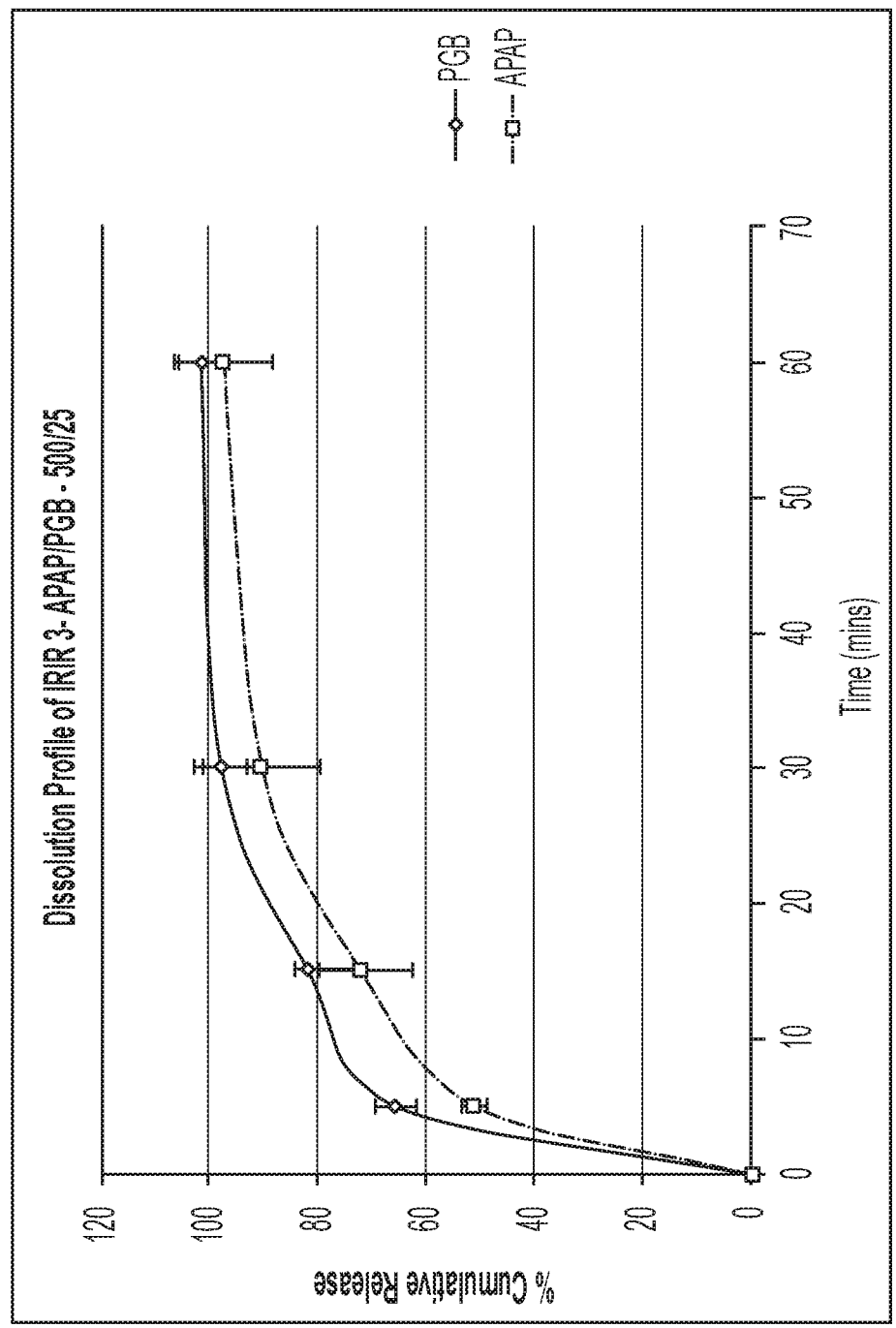
FIG. 11 depicts exemplary results for the release of APAP and PGB from bilayered caplets containing IRIR 3_APAP-500_PGB-25.
Figure 12:
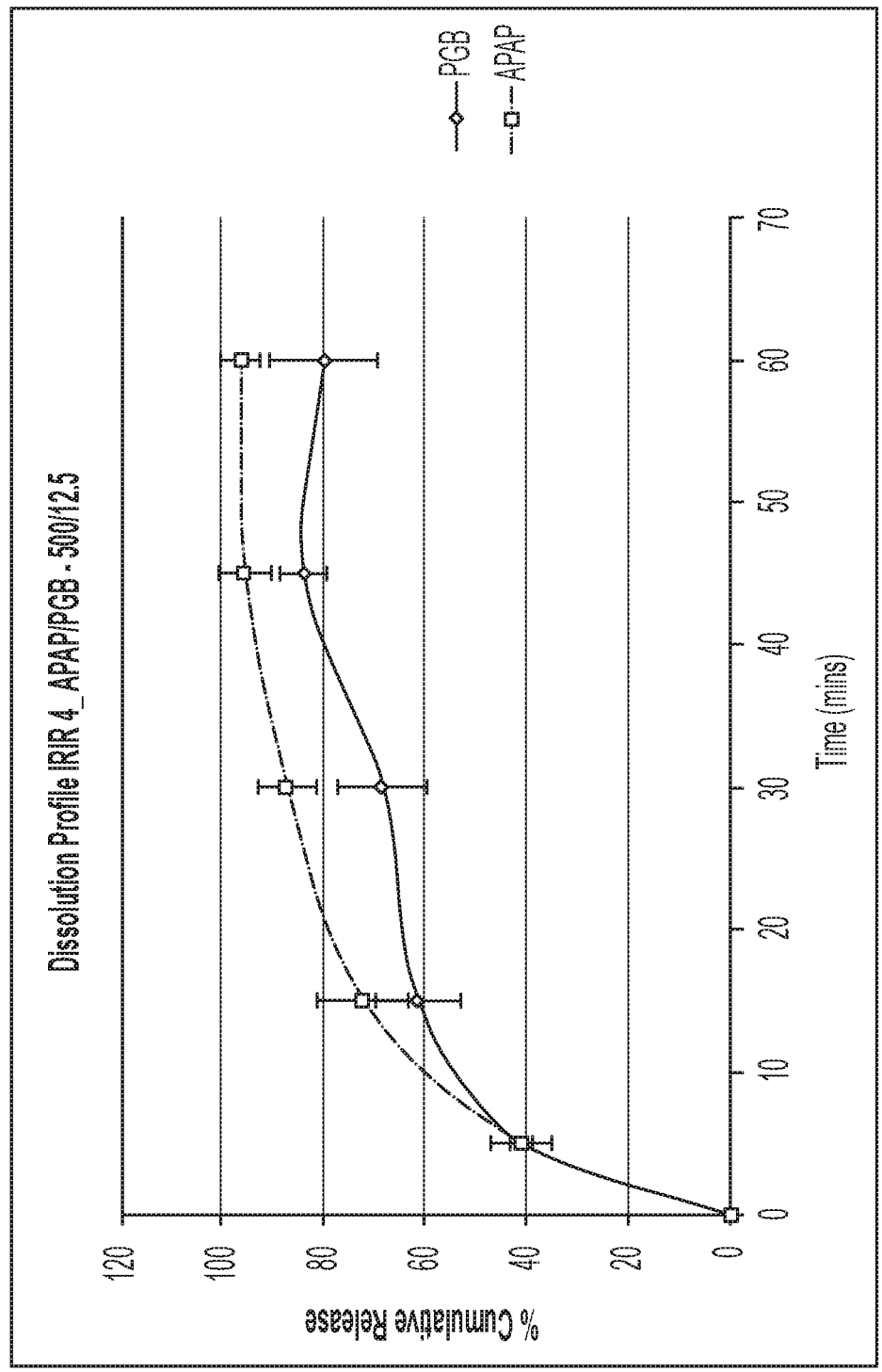
FIG. 12 depicts exemplary results for the release of APAP and PGB from bilayered caplets containing IRIR 3_APAP-500_PGB-12.5.

FIG. 11 depicts exemplary results for the release of APAP and PGB from bilayered caplets containing IRIR 3_APAP-500 PGB-25 (n=3 tablet, represented as average±S.D), and FIG. 12 depicts exemplary results for the release of APAP and PGB from bilayered caplets containing IRIR 3_APAP-500 PGB-12.5 (n=3 tablet, represented as average±S.D).

Exemplary fixed-dose combination drugs with acetaminophen and pregabalin in a formulation for immediate release of pregabalin and sustained release of acetaminophen: For these formulations, the following general protocol was used to produce the bilayered caplets:

Total weight of the caplet was set to be 1150 mg. Of the 1150 mg, API contributes 675 mg (650 APAP+25 PGB mg), which leaves about 475 mg for excipients. In this case, APAP extended release (ER) layer was assigned 850 mg and PGB immediate release (IR) was assigned 300 mg, and 5% HPMC E5 solution in water was used as a binder in the quantities shown in more detail below. APAP and diluent (Avicel PH102) were mixed in a mortar and using HPMC (5%), wet mass was passed using sieve #18-mesh (1 µm) to prepare the granules. Granules were dried at 400° C. for 30 mins. Later, the dried granules were sieved through #60 mesh screen to separate the fines. The weights of the granules (retained on mesh #60) and fines were recorded. Magnesium stearate and talc were mixed the total mixture to lubricate the granules and fines to provide granules for Layer 1(L1). Pregabalin (PGB) was incorporated extragranularly, hence Avicel PH102 granules were prepared initially. placebo granules (layer 2, L2), wet mass of Avicel PH102 was prepared using HPMC (5%) and processed in the same way as mentioned above and the PGB was added to the Avicel granules. 850 mg sample (L1) was individually weighed and compressed at thickness (3 mm tablet thickness, Kambert Mini Rotary tableting machine 8 station, using Natoli 06-124 D#483057; 0.3937×0.7480 CAPSULE SHAPE) and the same tablet was pushed in the die. 300 mg Layer 2 granules were placed above the tablet and compressed (3 mm tablet thickness) to provide a 1150 mg bilayered caplet. Tables 18-20 depict exemplary formulations.

TABLE 18

| Ingredient | Batch 002/027 | |
| --- | --- | --- |
| | APAP (mg/tab) | PGB (mg/tab) |
| APAP | 650 | 25 |
| Avicel PH 102 | 113.5 | 253 |
| Mg stearate | 17 | 6 |
| Talc | 17 | 6 |
| Methocel K4M HHP | 42.5 (5%) | — |
| Methocel E5 (binder) | 10 | 10 |

TABLE 19

| Ingredient | Batch 002/015 | |
| --- | --- | --- |
| | APAP (mg/tab) | PGB (mg/tab) |
| APAP | 650 | 50 |
| Avicel PH 102 | 113.5 | 236.5 |
| Mg stearate | 17 | 6 |
| Talc | 17 | 6 |
| Methocel K4M HHP | 42.5 (10%) | — |
| Methocel E5 (binder) | 10 | 7.5 |

TABLE 20

| Ingredient | Batch 002/001 | |
| --- | --- | --- |
| | APAP (mg/tab) | PGB (mg/tab) |
| APAP | 650 | 50 |
| Avicel PH 102 | 113.5 | 236.5 |
| Mg stearate | 17 | 6 |
| Talc | 17 | 6 |
| Methocel K4M HHP | 42.5 (10%) | — |
| Methocel E5 (binder) | 10 | 7.5 |

Figure 13A:
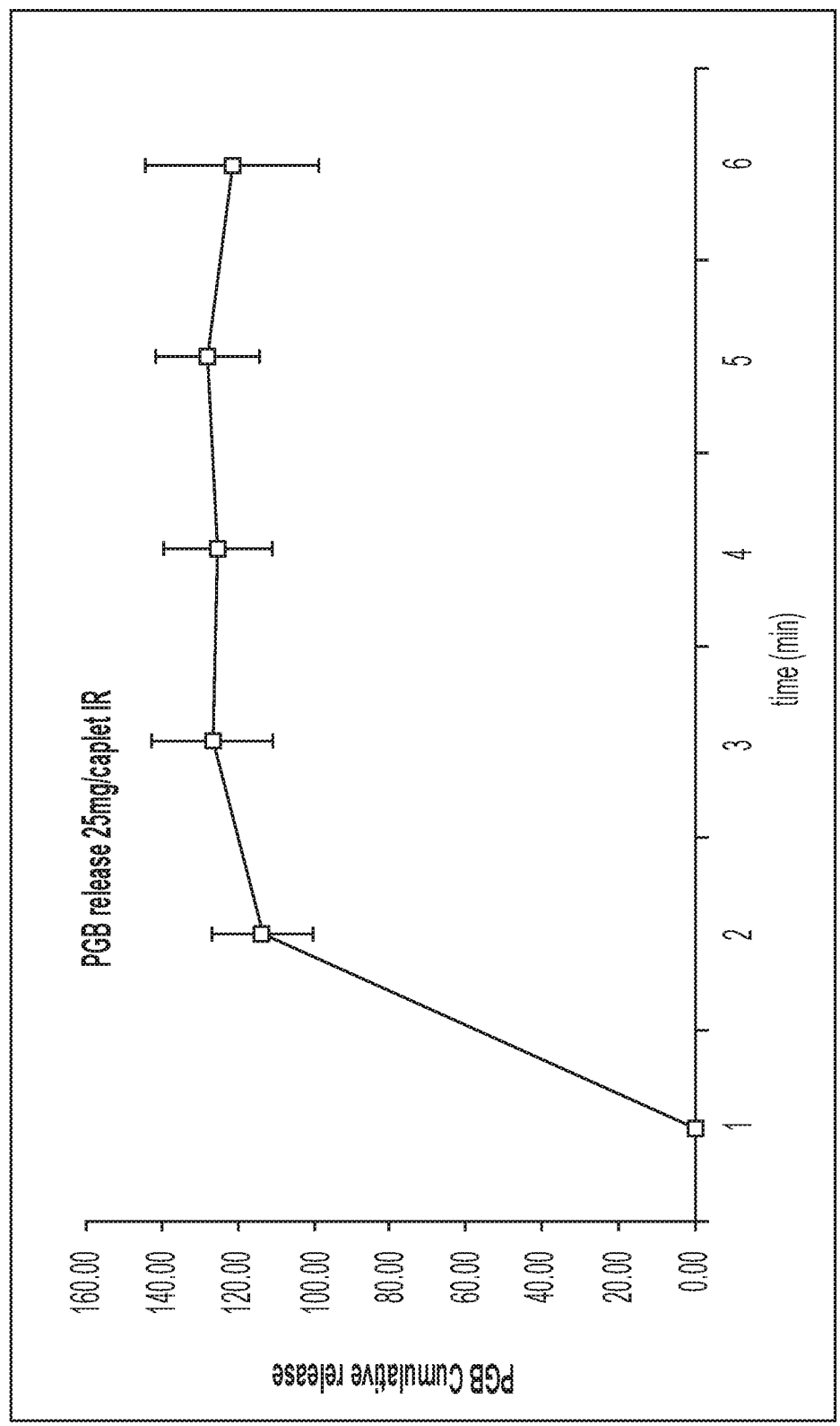
FIG. 13A depicts exemplary results for the release of 25mg/caplet PGB from Layer 2 of Bilayered Caplet containing Acetaminophen (ER) using 5% Methocel in layer 1.
Figure 13B:
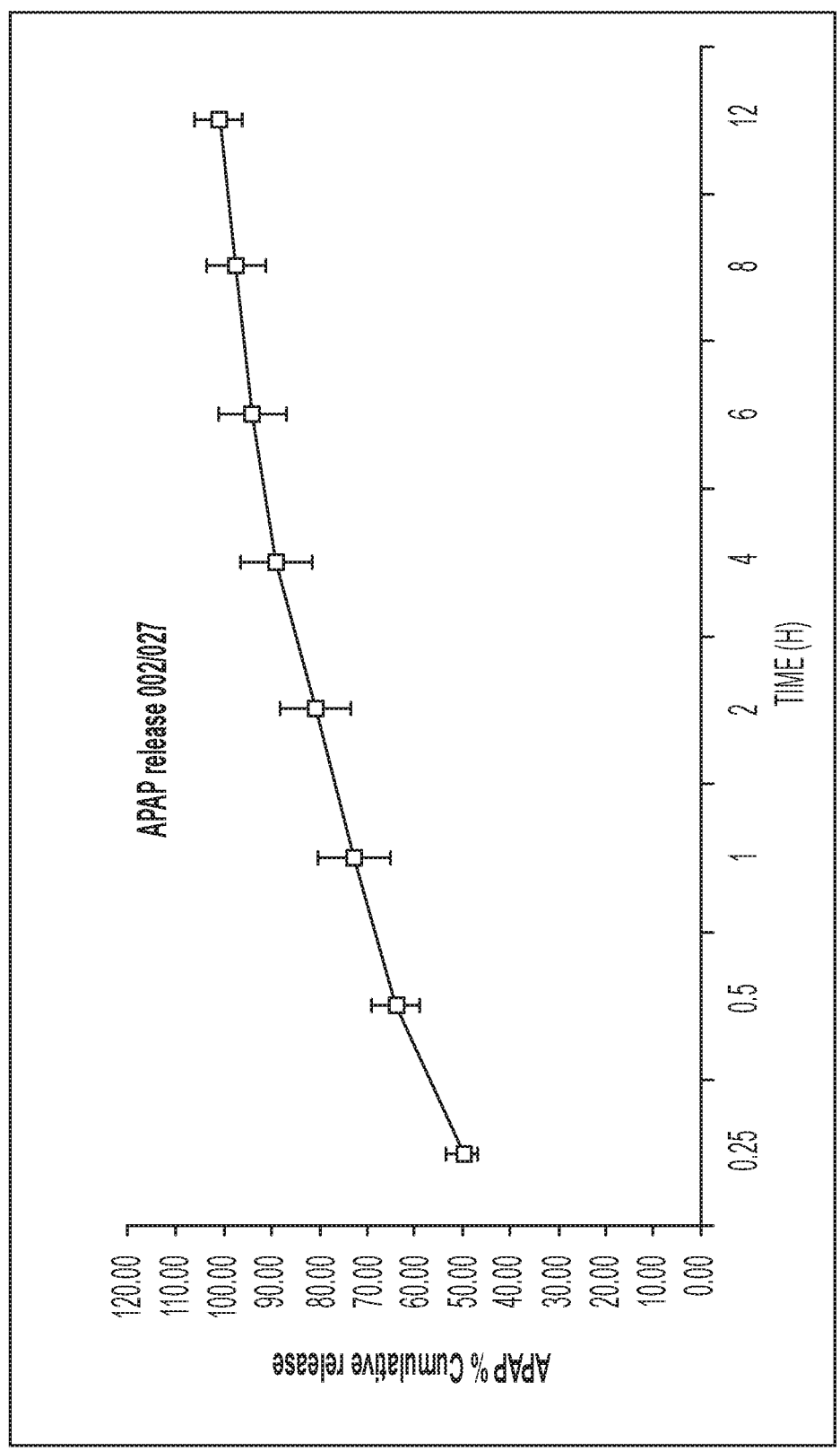
FIG. 13B depicts exemplary results for the release of APAP from Layer 1 of Bilayered Caplet containing using 5% Methocel as release retardant.
Figure 14A:
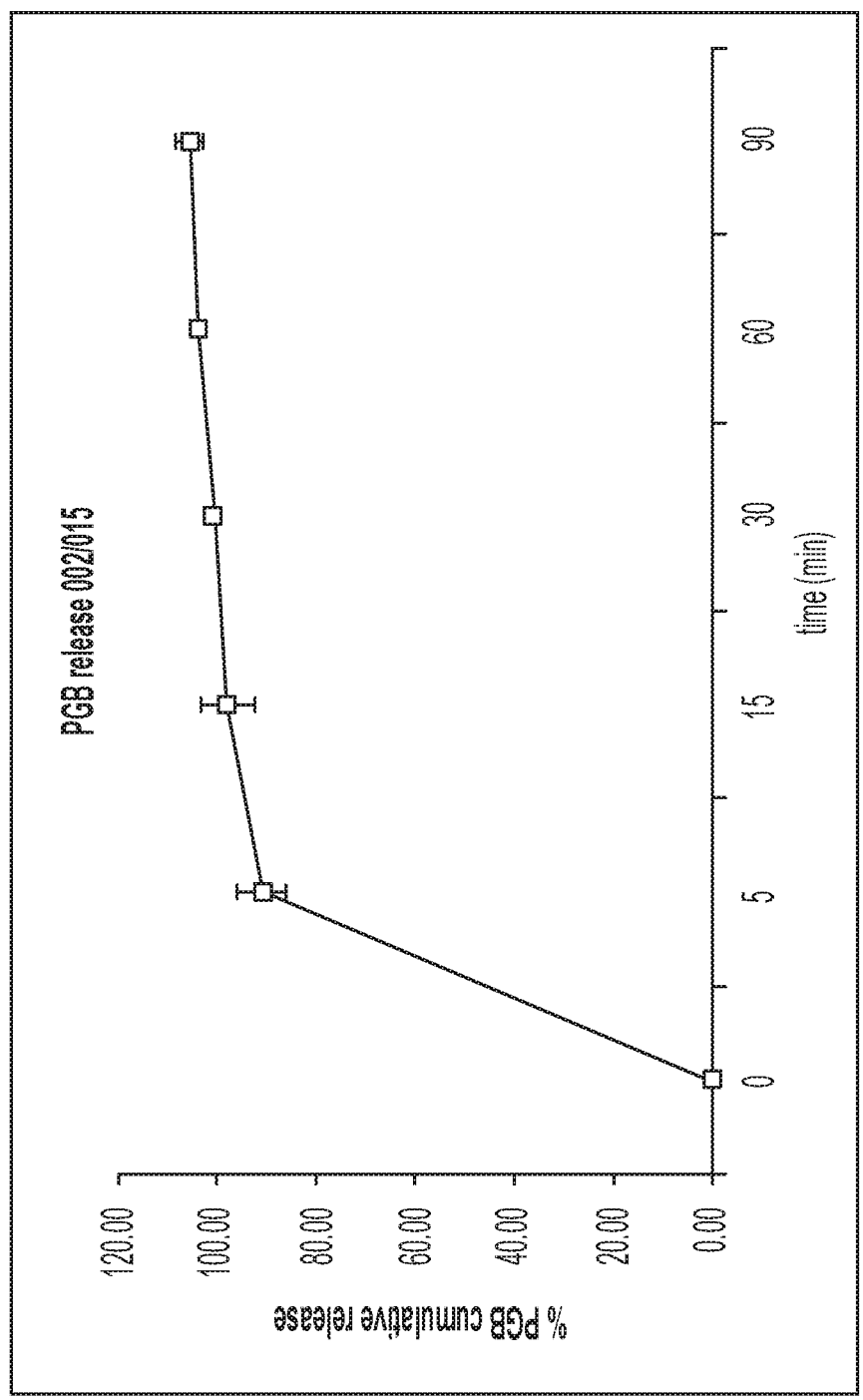
FIG. 14A depicts exemplary results for the release of PGB (37.5mg/tablet) from Layer 2 of Bilayered Caplet containing Acetaminophen (ER) using 5% Methocel in layer 1.
Figure 14B:
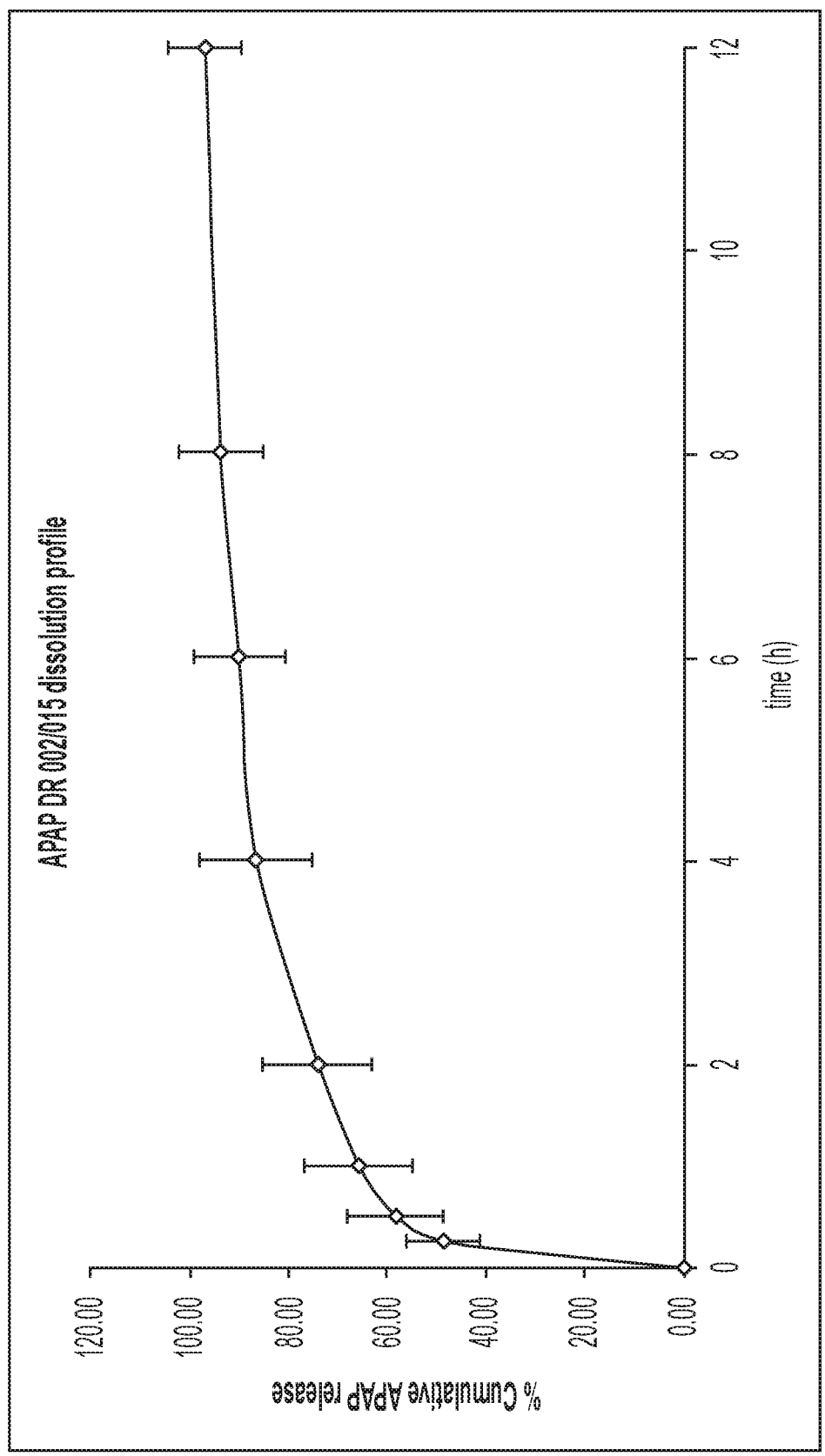
FIG. 14B depicts exemplary results for the release of APAP from Layer 1 of Bilayered Caplet containing using 5% Methocel as release retardant.
Figure 15A:
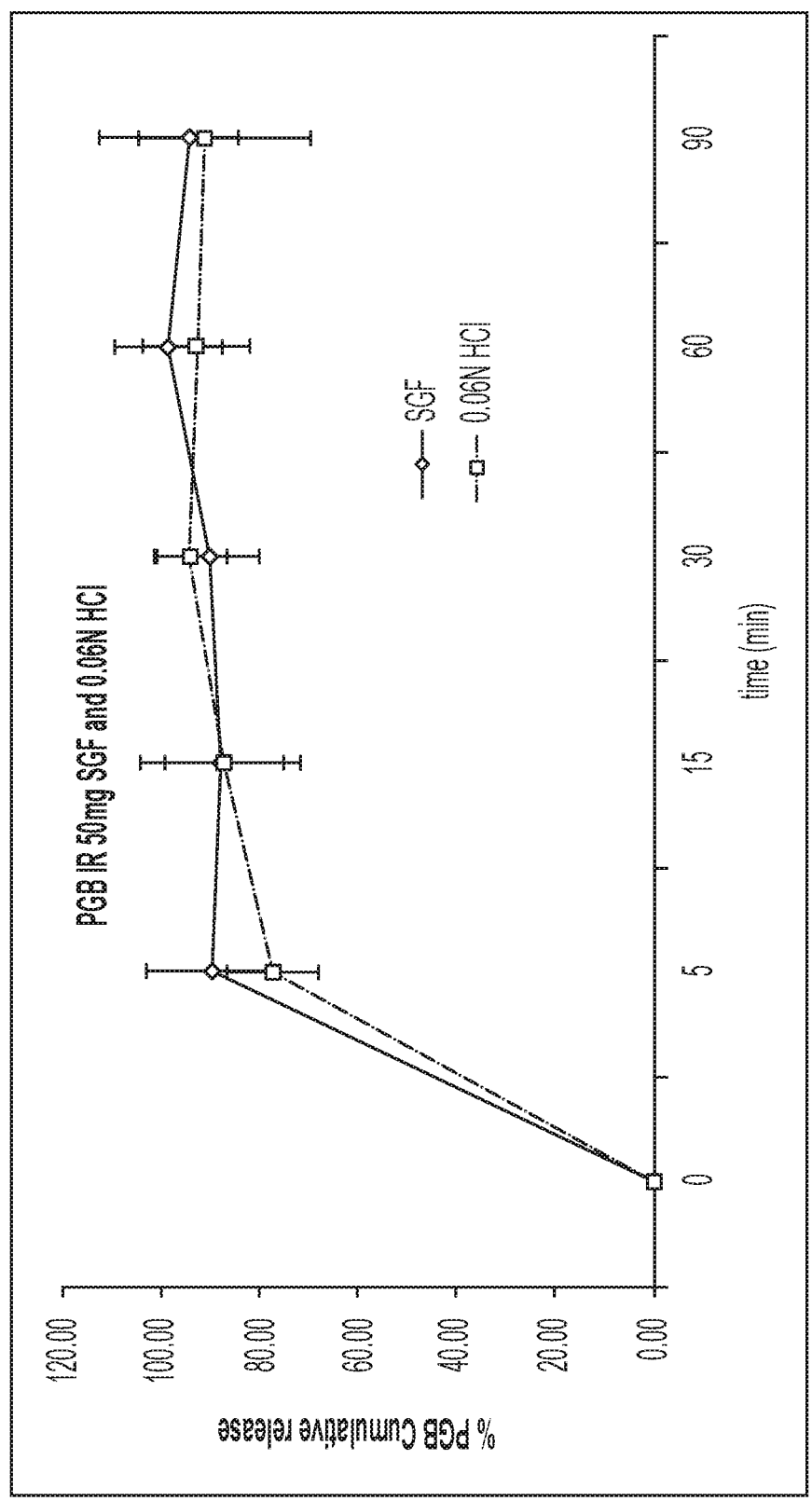
FIG. 15A depicts exemplary results for the release of PGB in simulated gastric fluid and 0.06N HCl from Layer 2 of Bilayered Caplet containing Acetaminophen (ER) using 5% Methocel in layer 1.
Figure 15B:
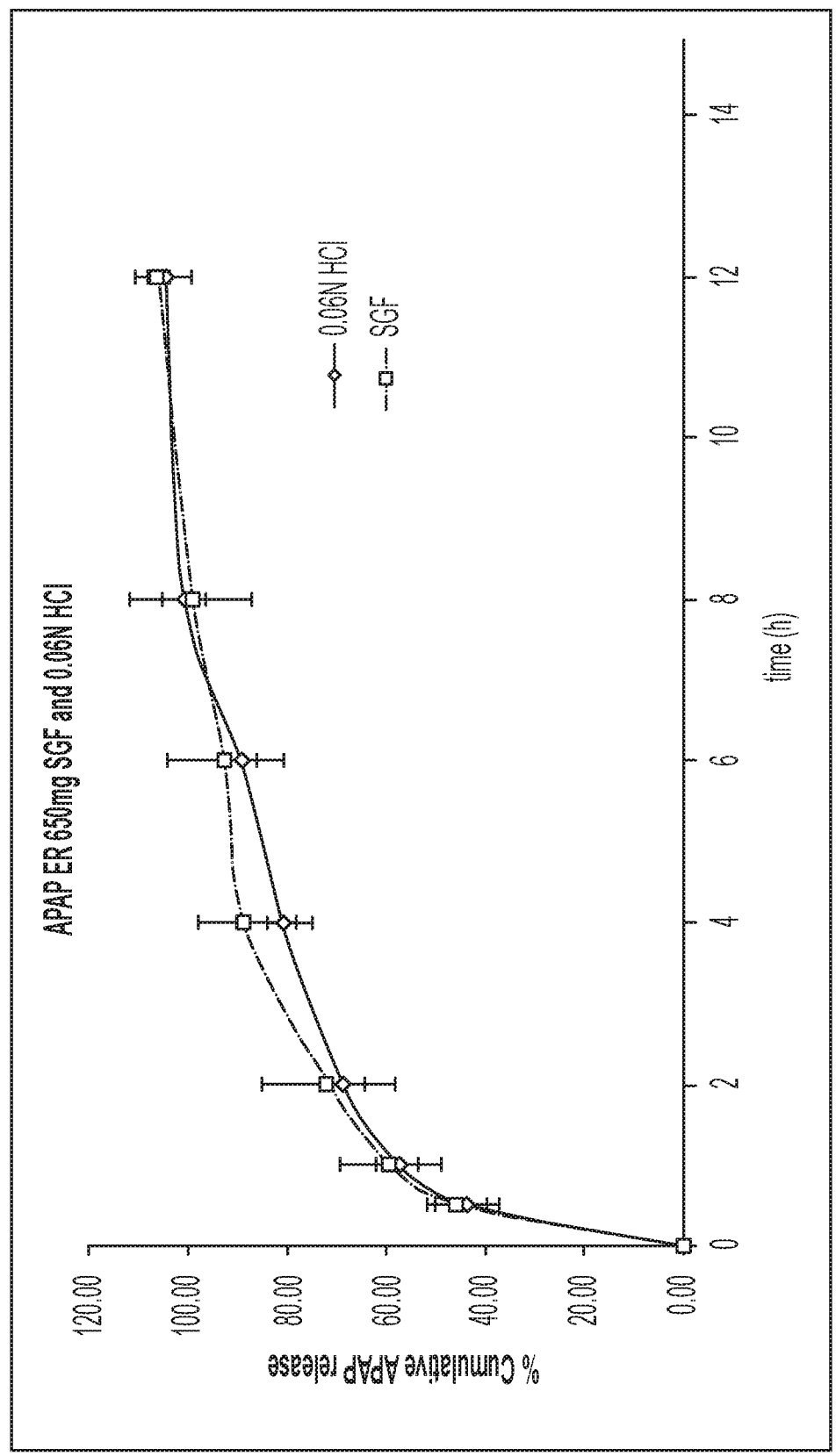
FIG. 15B depicts exemplary results for the release of APAP in simulated gastric fluid and 0.06N HCl from Layer 1 of Bilayered Caplet containing using 5% Methocel as release retardant.

FIG. 13A depicts exemplary results for the release of 25 mg/caplet PGB from Layer 2 of Bilayered Caplet containing Acetaminophen (ER) using 5% Methocel in layer 1 (002/027) (n=3 tablet, represented as average±S.D), and FIG. 13B depicts exemplary results for the release of APAP from Layer 1 of Bilayered Caplet containing using 5% Methocel as release retardant (002/027) (n=3 tablet, represented as average±S.D). FIG. 14A depicts exemplary results for the release of PGB (37.5mg/tablet) from Layer 2 of Bilayered Caplet containing Acetaminophen (ER) using 5% Methocel in layer 1 (002/015) (n=3 tablet, represented as average±S.D), and FIG. 14B depicts exemplary results for the release of APAP from Layer 1 of Bilayered Caplet containing using 5% Methocel as release retardant (002/015) (n=3 tablet, represented as average±S.D). FIG. 15A depicts exemplary results for the release of PGB in simulated gastric fluid and 0.06N HCl from Layer 2 of Bilayered Caplet containing Acetaminophen (ER) using 5% Methocel in layer 1 (002/001) (n=3 tablet, represented as average±S.D), and FIG. 15B depicts exemplary results for the release of APAP in simulated gastric fluid and 0.06N HCl from Layer 1 of Bilayered Caplet containing using 5% Methocel as release retardant (002/001) (n=3 tablet, represented as average±S.D). As can be readily taken from the figures, controlled release (immediate for PG and sustained for APAP) can be achieved from a single bilayer caplet.

Exemplary fixed-dose combination drugs with acetaminophen and pregabalin in a formulation for sustained release of both acetaminophen and pregabalin. For these formulations, the following general protocol was used to produce the bilayered caplets:

Total weight of the caplet was set to be 1150mg. In this case, APAP sustained release layer was assigned 850 mg and PGB immediate release layer was assigned 300 mg. 5% HPMC E5 solution in water was used as a binder in the quantities shown in more detail below.

APAP and diluent (Avicel PH 102) were mixed in a mortar and using HPMC (5%), wet mass was passed using sieve #18-mesh (1 µm) to prepare the granules. Granules were dried at 400° C. for 30 mins. Later, the dried granules were sieved through #60 mesh screen to separate the fines. The weights of the granules (retained on mesh #60) and fines were recorded. Magnesium stearate and talc were mixed the total mixture to lubricate the granules and fines to provide granules for Layer 1(L1).

APAP and PGB were granulated with the diluent Avicel PH102 using 5% E5 Methocel solution as the binder. Other extragranular materials which included were sodium starch glycolate, Magnesium stearate and Talc. 850 mg sample (L1) was individually weighed and compressed at thickness (3 mm tablet thickness, Kambert Mini Rotary tableting machine 8 station, using Natoli 06-124 D#483057; 0.3937× 0.7480 CAPSULE SHAPE) and the same tablet was pushed in the die. 300 mg Layer 2 granules were placed above the tablet and compressed (3 mm tablet thickness) to provide a 1150 mg bilayered caplet, and Table 21 lists exemplary ingredients used.

TABLE 21

IRIR_APAP_PGB-500/37.5

| Ingredient | Layer I - APAP | LAYER 2 - PGB |
|---|---|---|
| APAP | 650 | |
| PGB | | 25 |
| Mg stearate | 17 | 6 |
| Talc | 17 | 6 |
| E5- HPMC | 12 | 9 |
| K4 HHP Methocel * | 42.5 | 30 |
| AVICEL PH 102 | 111.5 | 224 |
| Final weight in layers (mg) | 850 | 300 |
| Total Caplet weight | | 1150 |

FIG. 16A depicts exemplary results for the release of 25 mg/caplet PGB from Layer 2 of Bilayered Caplet containing DRDR APAP-650 PGB-25 (n=3 tablet, represented as average±S.D), while FIG. 16B depicts exemplary results for the release of APAP from Layer 1 of Bilayered Caplet containing DRDR APAP-650 PGB-25 (n=3 tablet, represented as average±S.D). As can be readily taken from the figures, tailored and sustained release for PG and APAP can be achieved from a single bilayer caplet.

Of course, it should be appreciated that the release characteristics for the particular drugs need not be limited to those shown in the above examples, but that the release for immediate release of acetaminophen (or other NSAID) and pregabalin (or other GABA-type calcium channel blocker) can be tailored to any time between 0.1-0.5 min., 0.5-1 min., 1-2min., 2-5 min., 5-10 min., 10-20 min., or 20-45 min, or even longer. Similarly, and independently from the immediate release, the release for sustained release of acetaminophen (or other NSAID) and pregabalin (or other GABA-type calcium channel blocker) can be tailored to any time between 30 min-1 hour, 1-2 hrs., 2-4 hrs., 4-6 hours, 6-8 hrs, 8-12 hrs, 12-18 hrs, or 18-24 hrs., or even longer.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A fixed-dose combination drug, comprising:
   an NSAID (non-steroidal anti-inflammatory drug) as a first drug component in a first layer, and a GABA (gamma- aminobutyric acid)-type calcium channel blocker as a second drug component in a second layer;
   wherein the NSAID is acetaminophen and wherein the GABA (gamma-aminobutyric acid)-type calcium channel blocker is pregabalin;
   wherein the fixed-dose combination drug is formulated for oral administration such that a single oral dosage unit contains the first layer coupled and adjacent to the second layer, and wherein the fixed-dose combination drug provides upon oral administration in the single dosage unit to an individual in need thereof the NSAID in a sustained release in which cumulatively between 40-80% of the NSAID are released over a period of six to eight hours, and the GABA-type calcium channel blocker in a sustained release in which cumulatively between 40-80% of the GABA-type calcium channel blocker are released over a period of two hours.

2. The fixed-dose combination drug of claim 1, containing the NSAID in an amount of between 250 mg and 1500 mg.

3. The fixed-dose combination drug of claim 1, containing the NSAID in an amount of between 500 mg and 1300 mg.

4. The fixed-dose combination drug of claim 2, containing the GABA-type calcium channel blocker in an amount of between 5 mg and 600 mg.

5. The fixed-dose combination drug of claim 3, containing the GABA-type calcium channel blocker in an amount of between 10 mg and 600 mg.

6. The fixed-dose combination drug of claim 1, containing the GABA-type calcium channel blocker in an amount of between 5 mg and 100 mg.

7. The fixed-dose combination drug of claim 1, containing the GABA-type calcium channel blocker in an amount of between 10 mg and 50 mg.

8. The fixed-dose combination drug of claim 1, wherein cumulatively between 60-80% of the NSAID in the sustained release is released over a period of two hours.

9. The fixed-dose combination drug of claim 1, wherein cumulatively between 60-80% of the GABA-type calcium channel blocker in the sustained release is released over a period of six to eight hours.

\* \* \* \* \*